United States Patent
Ji et al.

(10) Patent No.: US 9,238,193 B2
(45) Date of Patent: Jan. 19, 2016

(54) SEPARATIONS WITH IONIC LIQUID SOLVENTS

(71) Applicants: Chevron Phillips Chemical Company LP, The Woodlands, TX (US); Chevron U.S.A. Inc., San Ramon, CA (US)

(72) Inventors: Lei Ji, Kingwood, TX (US); Ai-Fu Chang, Humble, TX (US); Michael S. Driver, Oakland, CA (US); Hye-Kyung Timken, Albany, CA (US)

(73) Assignees: CHEVRON PHILLIPS CHEMICAL COMPANY LP, The Woodlands, TX (US); CHEVRON U.S.A. INC., San Ramon, CA (US)

( * ) Notice: Subject to any disclaimer, the term of this patent is extended or adjusted under 35 U.S.C. 154(b) by 273 days.

(21) Appl. No.: 13/948,861

(22) Filed: Jul. 23, 2013

(65) Prior Publication Data

US 2015/0030524 A1    Jan. 29, 2015

(51) Int. Cl.
*B01D 53/78* (2006.01)
*B01D 53/62* (2006.01)
(Continued)

(52) U.S. Cl.
CPC ............ *B01D 53/1468* (2013.01); *B01D 53/14* (2013.01); *B01D 53/1475* (2013.01); *B01D 53/1487* (2013.01); *B01D 53/52* (2013.01); *B01D 53/62* (2013.01); *B01D 53/72* (2013.01); *B01D 53/78* (2013.01); *C01B 17/167* (2013.01); *C01B 31/20* (2013.01); *C07C 7/11* (2013.01);
(Continued)

(58) Field of Classification Search
CPC .... C07C 7/14875; C07C 7/144; C07C 7/152; C07C 7/156; C07C 9/12; C07C 11/64; B01D 53/78; B01D 53/62; B01D 53/52; B01D 53/72

See application file for complete search history.

(56) References Cited

U.S. PATENT DOCUMENTS

| 5,401,300 A | 3/1995 | Lokhandwala et al. |
| 5,407,467 A | 4/1995 | Lokhandwala et al. |

(Continued)

FOREIGN PATENT DOCUMENTS

| DE | 10333546 | 2/2005 |
| DE | 10333546 A1 | 2/2005 |

(Continued)

OTHER PUBLICATIONS

International Application PCT/US2014/046842 Invitation to Pay Additional Fees Partial International Search dated Oct. 15, 2014.

(Continued)

*Primary Examiner* — Timothy Vanoy
(74) *Attorney, Agent, or Firm* — Conley Rose, P.C.; Rodney B. Carroll; Monte R. Rhodes

(57) ABSTRACT

Disclosed are systems and methods which provide a process stream comprising a gaseous component, capture the gaseous component from the process stream by an ionic liquid solvent of a separator, and recover a captured gaseous component from the ionic liquid solvent in a regenerator. A second gaseous component from the process stream may be captured by the ionic liquid solvent of the separator, and the second gaseous component may be recovered from the ionic liquid solvent in the regenerator. Alternatively, the second gaseous component from the process stream may be uncaptured by the ionic liquid solvent, and the uncaptured second gaseous component may be recovered from a membrane unit.

44 Claims, 2 Drawing Sheets

(51) Int. Cl.
| | |
|---|---|
| *B01D 53/52* | (2006.01) |
| *B01D 53/72* | (2006.01) |
| *C07C 7/00* | (2006.01) |
| *B01D 53/14* | (2006.01) |
| *C01B 31/20* | (2006.01) |
| *C01B 17/16* | (2006.01) |
| *C07C 7/11* | (2006.01) |
| *C07C 7/144* | (2006.01) |
| *C07C 7/152* | (2006.01) |
| *C07C 7/156* | (2006.01) |
| *B01D 53/22* | (2006.01) |

(52) U.S. Cl.
CPC .............. *C07C 7/144* (2013.01); *C07C 7/152* (2013.01); *C07C 7/156* (2013.01); *B01D 53/1462* (2013.01); *B01D 53/229* (2013.01); *B01D 53/526* (2013.01); *B01D 2252/30* (2013.01); *B01D 2256/22* (2013.01); *B01D 2256/24* (2013.01); *B01D 2257/304* (2013.01); *B01D 2257/504* (2013.01); *B01D 2257/7022* (2013.01)

(56) References Cited

U.S. PATENT DOCUMENTS

| | | |
|---|---|---|
| 5,556,449 A | 9/1996 | Baker et al. |
| 5,558,698 A | 9/1996 | Baker et al. |
| 5,980,609 A | 11/1999 | Baker et al. |
| 6,339,182 B1 | 1/2002 | Munson et al. |
| 6,555,316 B1 | 4/2003 | Cohen et al. |
| 6,572,678 B1 | 6/2003 | Wijmans et al. |
| 6,623,659 B2 | 9/2003 | Munson et al. |
| 6,849,774 B2 * | 2/2005 | Boudreau et al. ............. 585/809 |
| 7,479,227 B2 | 1/2009 | Da Costa et al. |
| 7,619,129 B2 | 11/2009 | De Jong et al. |
| 7,799,299 B2 * | 9/2010 | Heldebrant et al. .......... 423/220 |
| 8,318,114 B2 | 11/2012 | Blair et al. |
| 8,398,748 B2 | 3/2013 | Mak |
| 2002/0063240 A1 | 5/2002 | Munson et al. |
| 2002/0189444 A1 | 12/2002 | Brennecke et al. |
| 2003/0125599 A1 | 7/2003 | Boudreau et al. |
| 2004/0099138 A1 | 5/2004 | Karode et al. |
| 2006/0251558 A1 * | 11/2006 | Chinn et al. .................. 423/230 |
| 2008/0112866 A1 | 5/2008 | Davis |
| 2010/0030007 A1 | 2/2010 | Lee et al. |
| 2010/0228035 A1 * | 9/2010 | Davis, Jr. .................... 546/278.4 |
| 2011/0015461 A1 * | 1/2011 | Dai et al. ...................... 585/818 |
| 2011/0213191 A1 * | 9/2011 | Schucker et al. ............. 585/845 |
| 2011/0223093 A1 * | 9/2011 | Scialdone .................. 423/437.1 |
| 2012/0232232 A1 | 9/2012 | Hottovy et al. |
| 2013/0255496 A1 * | 10/2013 | Zhang et al. ..................... 95/179 |
| 2013/0338389 A1 * | 12/2013 | Dai et al. ....................... 556/110 |
| 2015/0087866 A1 | 3/2015 | do Carmo et al. |

FOREIGN PATENT DOCUMENTS

| | | |
|---|---|---|
| EP | 2016991 A1 | 1/2009 |
| EP | 2751056 A2 | 7/2014 |
| GB | 2383328 | 6/2003 |
| WO | 0198239 | 12/2001 |
| WO | 03062171 | 7/2003 |
| WO | 2005061422 | 7/2005 |
| WO | WO2005075056 A1 | 8/2005 |
| WO | 2013030677 A2 | 3/2013 |
| WO | 2015013076 A1 | 1/2015 |

OTHER PUBLICATIONS

International Application PCT/US2014/046842 International Search Report dated Jan. 5, 2015.
Galán Sánchez, Lara M., et al., "Potential of silver-based room-temperature ionic liquids for ethylene/ethane separation," Ind. Eng. Chem. Res., 2009, pp. 10650-10656, vol. 48, No. 23, American Chemical Society.
Gas Processors Suppliers Association, "Engineering data book," vol. II, Sections 17-26, Tenth Edition, 1987, p. 19-32 and cover page, Gas Processors Association.
Camper, Dean, et al., "Low pressure hydrocarbon solubility in room temperature ionic liquids containing imidazolium rings interpreted using regular solution theory," Ind. Eng. Chem. Res., 2005, pp. 1928-1933, vol. 44, No. 6, American Chemical Society.
Worley Parsons brochure entitled "Tail gas unit description," Section 3, pp. 3-1 to 3-3. No Date.
Fallanza, Marcos, et al., "Screening of RTILs for propane/propylene separation using COSMO-RS methodology," Chemical Engineering Journal, 2013, pp. 284-293, vol. 220, Elsevier B.V.
Filing receipt and specification for patent application entitled "Separations with Ionic Liquid Solvents," by Lei Ji, et al., filed Jan. 15, 2015 as U.S. Appl. No. 14/597,415.
Foreign communication from a related counterpart application—International Search Report and Written Opinion, PCT/US2014/046842, Jan. 5, 2015, 16 pages.
Son, Seung J., et al., "Selective Absorption of Isoprene from $C_5$ Mixtures by $\pi$ Complexation with Cu(I)," Ind. Eng. Chem. Res., 2005, pp. 4717-4720, vol. 44, No. 13, American Chemical Society.
Foreign communication from a related counterpart application—International Search Report, PCT/US2015/011558, Apr. 29, 2015, 4 pages.

* cited by examiner

SEPARATIONS WITH IONIC LIQUID SOLVENTS

STATEMENT REGARDING FEDERALLY SPONSORED RESEARCH OR DEVELOPMENT

Not applicable.

REFERENCE TO A MICROFICHE APPENDIX

Not applicable.

FIELD

The disclosure relates to the separation of one or more gaseous components from a process stream using an ionic liquid solvent.

BACKGROUND

There are many process streams in commercial processing facilities, including facilities in the chemical, petrochemical, polymerization, oil, and gas industries, which contain two or more fluid components. Examples of process streams containing two or more fluid components include: polymerization process streams, ethane cracker process streams, natural gas process streams, syngas process streams, biomass gasification process streams, Fischer-Tropsch process streams, alkane dehydrogenation process streams, and alcohol dehydration process streams. Sometimes it is desirable to separate the fluid components of a process stream so as to "upgrade" the process stream and/or to recover a fluid component of value.

Separation techniques include conventional distillation, absorption using ionic liquid membranes, and absorption using aqueous solutions of metal salts. Distillation requires a large number of stages and/or high reflux ratios when fluid components have close boiling points and can be cost-prohibitive. Ionic liquid membranes are limited by membrane diffusion rates and can have poor flux or require significant capital expenditure for commercial applications. The water in an aqueous solution of metal salts has a significant vapor pressure which makes recovery of the separated component from the aqueous solution inefficient (e.g., water is typically carried with the component after the component is separated from the aqueous solution, requiring de-watering).

There is an ongoing need for improved separation techniques for process streams in commercial processing facilities.

SUMMARY

The disclosed embodiments include a method comprising providing a process stream comprising a gaseous component; capturing at least a portion of the gaseous component from the process stream by an ionic liquid solvent; and recovering at least a portion of a captured gaseous component from the ionic liquid solvent. In embodiments, at least a portion of a second gaseous component from the process stream is captured by the ionic liquid solvent, and the method further comprises recovering at least a portion of the second gaseous component from the ionic liquid solvent. In embodiments, at least a portion of a second gaseous component from the process stream is uncaptured by the ionic liquid solvent, and the method further comprises recovering at least a portion of the uncaptured second gaseous component from a membrane unit.

The disclosed embodiments include a system comprising a process stream comprising a gaseous component; a separator comprising an ionic liquid solvent, wherein the separator receives the process stream, wherein the ionic liquid solvent captures at least a portion of the gaseous component; a captured stream exiting the separator and comprising the captured gaseous component captured in the ionic liquid solvent; and a regenerator to receive the captured stream, wherein the regenerator regenerates the ionic liquid solvent and emits the recovered gaseous component. In embodiments, the ionic liquid solvent further captures at least a portion of a second gaseous component from the process stream, the captured stream further comprises the captured second gaseous component, and the regenerator emits the recovered second gaseous component. In embodiments, the ionic liquid solvent does not capture at least a portion of a second gaseous component from the process stream, and the system further comprises an uncaptured stream exiting the separator and comprising the uncaptured second gaseous component. In embodiments, the system may further comprise a membrane unit to recover the second gaseous component.

The foregoing has outlined rather broadly the features and technical advantages of the disclosed inventive subject matter in order that the following detailed description may be better understood. The various characteristics described above, as well as other features, will be readily apparent to those skilled in the art upon reading the following detailed description of the preferred embodiments, and by referring to the accompanying drawings.

DESCRIPTION OF THE DRAWINGS

For a detailed description of the preferred embodiments of the disclosed processes and systems, reference will now be made to the accompanying drawings in which.

DETAILED DESCRIPTION

Disclosed herein are embodiments of systems and methods related to the separation of one or more gaseous components from a process stream using an ionic liquid solvent, resulting in recovery of the gaseous component, for example, to improve process efficiency (e.g., to avoid recycle of the gaseous component) or for use of the gaseous component (e.g., to avoid wasteful flaring of a valuable gaseous component).

The disclosed embodiments may be utilized in conjunction with any process stream suitable for gaseous component separation utilizing an ionic liquid solvent. Examples of process streams comprising gaseous components which can be separated from other fluid components include: polymerization process streams comprising olefins and alkanes; ethane cracker process streams comprising ethane and ethylene; natural gas process streams comprising natural gas and an acid gas; syngas process streams comprising syngas and carbon dioxide; biomass gasification process streams comprising carbon dioxide; Fischer-Tropsch process streams comprising unreacted syngas, methane, olefins, and alkanes; alkane dehydrogenation process streams comprising olefins and alkanes; alcohol dehydration process streams comprising olefins, alkanes, and alcohols; etc.

The embodiments disclosed herein are discussed in the context of a process stream comprising a gaseous component which includes i) an olefin and/or an alkane, or ii) an acid gas (e.g., $CO_2$ and/or $H_2S$).

"Gaseous component" may refer to an olefin, an alkane, an acid gas, one or more components of a natural gas process stream, one or more components of a syngas process stream, hydrogen, nitrogen, oxygen, water, carbon monoxide, oxygenates (e.g., alcohols), or combinations thereof.

"Olefin" may refer to a $C_2$-$C_{50}$ hydrocarbon having a carbon-carbon double bond. Suitable olefins may include other functional groups, such as hydroxy groups, carboxylic acid groups, heteroatoms, and the like, provided that such groups do not react with the ionic liquid solvent. Embodiments disclosed herein are described using ethylene as the olefin.

"Alkane" may refer to $C_2$-$C_{50}$ hydrocarbons which are saturated. Embodiments disclosed herein are described using ethane and/or isobutane.

"Acid gas" may refer to $CO_2$, $H_2S$, RSH, $CS_2$, COS, and $SO_2$, or combinations thereof. Embodiments disclosed herein are described using $CO_2$ and $H_2S$.

Figure 1:
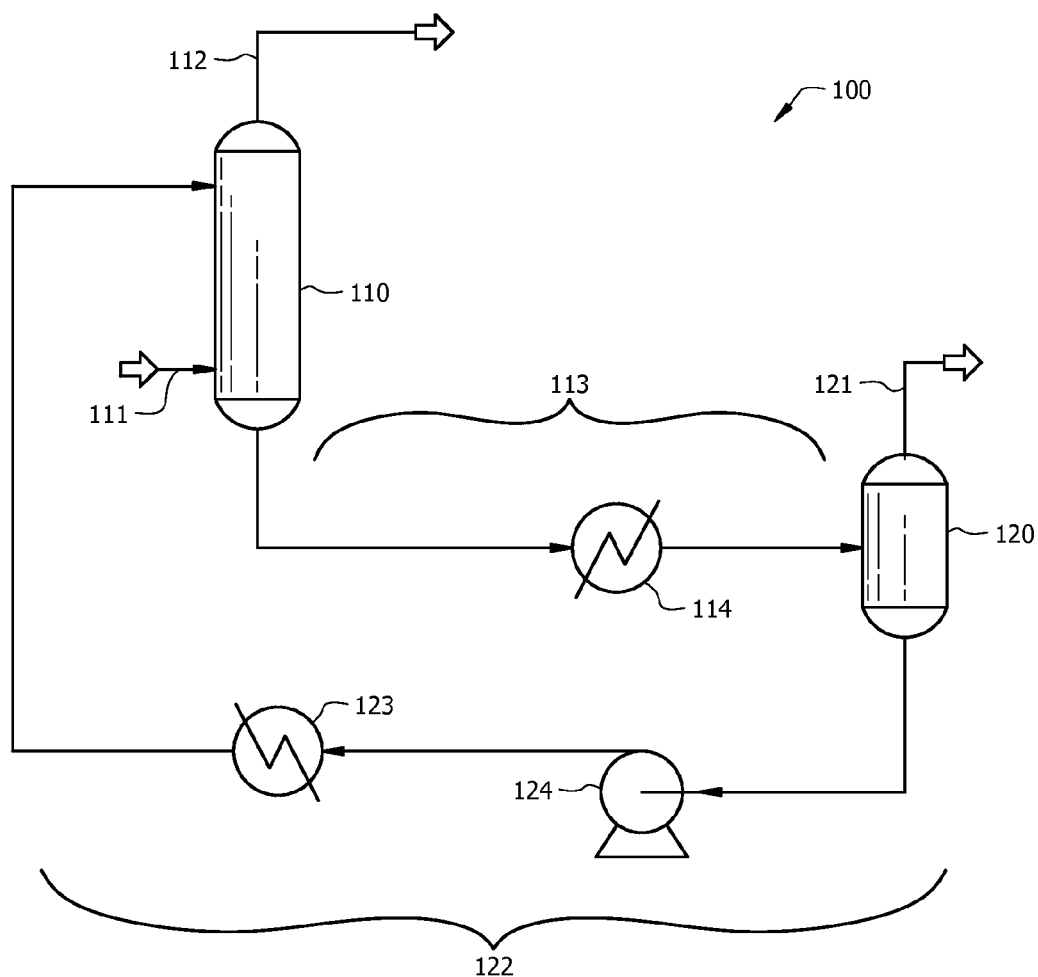
FIG. 1 illustrates a process flow diagram of an embodiment of the disclosed system.

FIG. 1 shows a process flow diagram of an embodiment of the disclosed system 100. The system 100 may comprise a separator 110 and a regenerator 120. A process stream 111 comprising a gaseous component (optionally, a second gaseous component) may feed to the separator 110, which receives the process stream 111. The separator 110 may comprise an ionic liquid solvent, and the ionic liquid solvent may capture at least a portion of the gaseous component (optionally, at least a portion of the second gaseous component). A captured stream 113 comprising the gaseous component (optionally, the second gaseous component) captured by the ionic liquid solvent may exit from the separator 110 and flow to the regenerator 120, and the regenerator 120 may receive the captured stream 113. A portion of the process stream 111 which is not captured by the ionic liquid solvent in the separator 110 may exit the separator 110 and flow through uncaptured stream 112 for further processing, use, sale, flare, etc. The regenerator 120 may regenerate the ionic liquid solvent and emit the recovered gaseous component (optionally, recovered second gaseous component). The recovered gaseous component (optionally, recovered second gaseous component) may flow via stream 121 from the regenerator 120 for further processing, use, sale, etc. The regenerated ionic liquid solvent may flow from the regenerator 120 to the separator 110 through solvent stream 122. The ionic liquid solvent may generally circulate through a solvent circulation system comprising the separator 110, captured stream 113, the regenerator 120, and the solvent stream 122. The captured stream 113 may comprise a heater 114 capable of heating the captured stream 113 as the captured gaseous component (optionally, captured second gaseous component) flows to the regenerator 120. The solvent stream 122 may comprise a cooler 123 capable of cooling the solvent stream as the regenerated ionic liquid solvent flows to the separator 110, and a pump 124 for providing a motive force for flowing the regenerated ionic liquid solvent. The system 100 may further comprise one or more compressors, pumps, heat exchangers, valves, control devices, safety devices, or similar apparatuses, not shown in FIG. 1. Such apparatuses may be included in system 100 according to techniques recognized by one skilled in the art with the aid of this disclosure.

In embodiments, the gaseous component of the process stream 111 may comprise ethylene, isobutane, or an acid gas (e.g., $CO_2$ and/or $H_2S$). In additional embodiments, the second gaseous component of the process stream 111 may comprise ethylene, isobutane or an acid gas (e.g., $CO_2$ and/or $H_2S$). As described above, the process stream 111 may comprise a second gaseous component, and the ionic liquid solvent may capture at least a portion of the second gaseous component. In embodiments, the capture of at least a portion of the second gaseous component is in addition to the capture of at least a portion of the gaseous component. In an embodiment, the gaseous component comprises ethylene and the second gaseous component comprises isobutane. In an alternative embodiment, the gaseous component comprises carbon dioxide, and the second gaseous component comprises hydrogen sulfide.

In an embodiment, the ionic liquid solvent may capture at least a portion of the gaseous component; additionally or alternatively, the ionic liquid solvent may capture at least a portion of the second gaseous component; additionally or alternatively, the ionic liquid solvent may not capture at least a portion of the second gaseous component.

In embodiments, the ionic liquid solvent may capture the gaseous component and/or the second gaseous component via various mechanisms of capture. In an embodiment, at least a portion of the gaseous component is captured by the ionic liquid solvent via absorption, dissolution, adsorption, complexation, or combinations thereof. In an additional embodiment, at least a portion of the second gaseous component is captured by the ionic liquid solvent via absorption, dissolution, adsorption, complexation, or combinations thereof. In embodiments, the mechanism of capture of the gaseous component is the same as the mechanism of capture for the second gaseous component. For example, the gaseous component and the second gaseous component may both be captured via absorption, adsorption, dissolution, or complexation. In an alternative embodiment, the mechanism of capture of the gaseous component is different than the mechanism capture for the second gaseous component. For example, the gaseous component may be captured via absorption and the second gaseous component may be captured via adsorption or dissolution. In another example, the gaseous component may be captured via absorption with complexation and the second gaseous component may be captured via absorption without complexation.

In embodiments, the process stream 111 may further comprise other fluid components such as other gaseous components. Other gaseous components of the process streams 111 may include hydrogen, nitrogen, ethane, natural gas, syngas, or combinations thereof.

In embodiments, the concentration of the gaseous component and/or the second gaseous component in the process stream 111 may comprise greater than about 10%, 20%, 30%, 40%, 50%, 60%, 70%, 80%, 90%, or greater by weight of the process stream 111.

In embodiments, the separator 110 may comprise a vessel configured to flow the ionic liquid solvent therethrough so as to selectively capture (e.g., absorb, adsorb, dissolve, complex, or combinations thereof) at least a portion of the gaseous component (optionally, a second gaseous component) from the process stream 111 comprising the gaseous component (optionally, the second gaseous component) and one or more other fluid (e.g., gaseous) components.

In an embodiment, the separator 110 may be configured to dissipate a gas (e.g., gaseous component, optionally second gaseous component, of process stream 111) within the ionic liquid solvent, for example, by bubbling the gas through the liquid. In an embodiment, the separator 110 may include a solvent circulation system configured to circulate the ionic liquid solvent through the separator 110. Non-limiting examples of suitable separator configurations include an absorption tower; a pressure-swing absorber (PSA); a sparger tank; an agitation reactor; a vessel coupled with one or more compressors, one or more pumps 124, and one or more heat exchangers (e.g., heater 114, cooler 123); or combinations thereof. An example of a suitable separator is illustrated in Gas Processors Association, *Engineering Data Book* 10th ed., at FIG. 19-46.

In an additional and/or alternative embodiment, the separator 110 may comprise a packed bed or column configured to maintain smaller bubble sizes (e.g., of the gas being dissipated within the ionic liquid solvent), for example, so as to maintain a relatively large surface area of contact between the gas and the ionic liquid solvent, for example, so as to maintain an efficiency of mass transfer and/or capture of the gas into the liquid. In an embodiment, the packing material of the packed bed or column may comprise a polymeric material, metallic material, or combinations thereof. In an embodiment, the separator 110 may have multiple packed beds or columns. In an embodiment, one or more sections of the separator 110 may have a packing material. In embodiments, the packing material may have a random packing or may have a structured packing.

In embodiments, the separator 110 may comprise two or more sections. For example, a first section may operate at a first set of conditions (e.g., temperature, pressure, flow rate, mass flow ratio), and a second section may operate at a second set of conditions (e.g., temperature, pressure, flow rate, mass flow ratio).

In embodiments, the separator 110 may function at times to capture, and at other times to uncapture, the gaseous component (optionally, second gaseous component). That is, the separator 110 may also function as a regenerator. In such embodiments, the temperature and pressure at which the separator 110 operates may depend upon the function. For example, the temperature and pressure of the separator 110 when operating to capture the gaseous component (optionally, second gaseous component) may be those disclosed herein for capturing the gaseous component (optionally, the second gaseous component). The temperature and pressure of the separator 110 when operating to liberate the gaseous component (optionally, the second gaseous component) may be those disclosed herein for the regenerator 120. In such embodiments, the separator 110 may additionally or alternatively be configured to evacuate one or more gases (e.g., a previously captured and then liberated gas, such as olefin, acid gas, alkane) and/or to facilitate the release of the captured gas via a pressure differential.

In embodiments, the separator 110 may be configured to provide or maintain a suitable partial pressure of a gaseous component of the process stream 111. Such a suitable partial pressure may be about 14.8 psia to about 57.7 psia; alternatively, about 19.7 psia to about 47.7 psia; alternatively, about 19.7 psia to about 29.7 psia. In an embodiment, the separator 110 may be configured to provide or maintain an ethylene partial pressure from about 0 psia to about 100 psia.

In an embodiment, the separator 110 may be configured for batch and/or continuous operation.

In embodiments, the system 100 may comprise two or more separators (e.g., separator 110 and one or more other separators). For example, the system 100 may comprise two separators, each of which may be configured according to one of the embodiments disclosed herein. Embodiments having two or more separators may be configured for pressure swing absorption (PSA) of the gaseous component (optionally, the second gaseous component). For example, by employing two or more separators, the system 100 may be configured to allow for continuous operation by absorbing the gaseous component (optionally, the second gaseous component) into a "first batch" in the first separator while a "second batch" is prepared for absorption in a second separator. As such, by cycling between two or more suitable separators, a system may operate continuously. An example of a system having two or more separators is disclosed in U.S. Patent Application Publication No. 2012/0232232, published on Sep. 13, 2012, entitled "Ethylene Recovery By Absorption," and incorporated herein by reference in its entirety.

In embodiments, the separator 110 may be configured to have a liquid-to-gas mass flow ratio from about 1 to about 350; alternatively, from about 1 to about 200; alternatively, from about 10 to about 200; alternatively, from about 10 to about 100. In embodiments, the liquid-to-gas mass flow ratio of the separator 110 may comprise a value such that at least a portion of the gaseous component is captured by the ionic liquid solvent. In additional or alternative embodiments, the liquid-to-gas mass flow ratio of the separator 110 may comprise a value such that at least a portion of the gaseous component and at least a portion of a second gaseous component are captured by the ionic liquid solvent. Generally, a mass flow ratio which captures at least a portion of the gaseous component and at least a portion of the second gaseous component is greater than a mass flow ratio which captures only at least a portion of the gaseous component. In embodiments, a mass flow ratio which captures at least a portion of the gaseous component and at least a portion of the second gaseous component is substantially greater (e.g., about 2 times, about 3 times, about 4 times, about 5 times, about 6 times, about 7 times, about 8 times, about 9 times, about 10 times, about 11 times, about 12 times, about 13 times, about 14 times, about 15 times, or more) than a mass flow ratio which captures only at least a portion of the gaseous component. In an embodiment, the "liquid" of the liquid-to-gas mass flow ratio may comprise the ionic liquid solvent; alternatively, the "liquid" of the liquid-to-gas mass flow ratio may comprise the ionic liquid solvent and any combination of other liquids flowing in and/or through the separator 110; alternatively, the "liquid" of the liquid-to-gas mass flow ratio may comprise the ionic liquid solvent and any combination of other liquids flowing in and/or through the solvent circulation system. In an embodiment, the "gas" of the liquid-to-gas mass flow ratio may comprise the gaseous component of the process stream 111; alternatively, the "gas" of the liquid-to-gas mass flow ratio may comprise the gaseous component and the second gaseous component of the process stream 111; alternatively, the "gas" of the liquid-to-gas mass flow ratio may comprise the any combination of gases flowing in and/or through the process stream 111 and/or the separator 110 (e.g., from the process stream 111, from all streams flowing into the separator 110, or from a combination of streams flowing into the separator 110).

In embodiments where the separator 110 comprises two or more sections, the two or more sections may operate at the same or different liquid-to-gas mass flow ratio. For example, a first section of the separator 110 may operate at a first liquid-to-gas mass flow ratio and a second section may operate at a second liquid-to-gas mass flow ratio, wherein the first liquid-to-gas mass flow ratio is different than the second liquid-to-gas mass flow ratio.

In an embodiment, the separator 110 may be capable of selectively inducing thermal and/or pressure fluctuations, variations, or cycles. For example, the separator 110 may cycle between temperatures and pressures for capturing the gaseous component (optionally, second gaseous component) and for uncapturing the gaseous component (optionally, second gaseous component).

In embodiments, a temperature or temperatures at which the separator 110 operates may depend upon the function of the separator 110 at a given time. For example, the separator 110 may be configured to provide or maintain a first temperature (e.g., one or more of those disclosed for operation of the separator 110) for the purpose of capturing the gaseous component (optionally, second gaseous component), and the separator 110 may be configured to provide or maintain a second temperature (e.g., one or more of those disclosed for operation of the regenerator 120) for the purpose of regenerating the ionic liquid solvent, recovering the recovered gaseous component (optionally, second recovered gaseous component), or both.

In embodiments where the separator 110 operates to capture the gaseous component (optionally, second gaseous component), the separator 110 may operate at a temperature from about 5° C. to about 50° C.; alternatively, from about 20° C. to about 40° C. In embodiments wherein the separator 110 operates to uncapture (i.e., liberate) the gaseous component (optionally, the second gaseous component), the separator 110 may operate at a temperature from about 60° C. to about 450° C., at a temperature greater than the temperature of the separator 110 when functioning in the capturing mode, or both.

In embodiments, a pressure or pressures at which the separator 110 operates may depend upon the function of the separator 110 at a given time. For example, the separator 110 may be configured to provide or maintain a first pressure (e.g., one or more of those disclosed for operation of the separator 110) for the purpose of capturing the gaseous component (optionally, second gaseous component), and the separator 110 may be configured to provide or maintain a second pressure (e.g., one or more of those disclosed for operation of the regenerator 120) for the purpose of regenerating the ionic liquid solvent, recovering the recovered gaseous component (optionally, second recovered gaseous component), emitting the recovered gaseous component (optionally, second recovered gaseous component), or combinations thereof.

In embodiments wherein the separator 110 operates to capture the gaseous component (optionally, the second gaseous component), the separator 110 may operate at a pressure from about 100 psia to about 250 psia. In embodiments wherein the separator 110 operates to uncapture (i.e., liberate) the gaseous component (optionally, the second gaseous component), the separator 110 may operate at a pressure greater than or equal to about 14.7 psia, at a pressure less (e.g., 20 psi less) than the pressure at which the separator 110 operates when capturing the gaseous component (optionally, second gaseous component), or both.

In embodiments, the ionic liquid solvent may generally comprise a cation, an anion, a Ag(I) salt, a Cu(I) salt, or combinations thereof. In an embodiment, the ionic liquid solvent may be capable of reversibly complexing, may be capable of absorbing, may be capable of adsorbing, may be capable of dissolving, or combinations thereof, at least a portion of the gaseous component of the process stream 111. In additional or alternative embodiments, the ionic liquid solvent may be capable of reversibly complexing, may be capable of absorbing, may be capable of adsorbing, may be capable of dissolving, or combinations thereof, at least a portion of the second gaseous component of the process stream 111.

In an embodiment, the ionic liquid solvent may comprise a liquid phase at 14.7 psia and 25° C. In an embodiment, the ionic liquid solvent may be referred to as a room temperature ionic liquid ("RTIL"). Ionic liquid solvents disclosed herein may comprise a negligible vapor pressure at operating conditions of the disclosed systems, resulting in negligible loss of the ionic liquid solvent during operation. Moreover, use of the ionic liquid solvents disclosed herein reduces VOC emissions.

In embodiments, the ionic liquid solvent may comprise a cation and an anion. In embodiments, the cation may comprise an ethylmethylimidazolium [emim] cation, a butylmethylimidazolium [bmim] cation, a butylmethylpyridinium [mebupyl] cation, or combinations thereof. In embodiments, the anion may comprise a bis(trifluoromethanesulfonyl)amide [$Tf_2N$] anion, a hexafluorophosphate [$PF_6$] anion, a trifluoromethanesulfonate [TfO] anion, a dicyanamide [DCA] anion, a tetrafluoroborate [$BF_4$] anion, a thiocyanate [SCN] anion, a nitrate [$NO_3$] anion, a sulfonate [$CF_3SO_3$] anion, a methylsulfate [$CH_3SO_4$] anion, or combinations thereof.

In embodiments, the ionic liquid solvent may comprise ethylmethylimidazolium bis(trifluoromethanesulfonyl) amide ([emim][$Tf_2N$]), butylmethylimidazolium hexafluorophosphate ([bmim][$PF_6$]), ethylmethylimidazolium trifluoromethanesulfonate ([emim][TfO]), ethylmethylimidazolium dicyanamide ([emim][DCA]), butylmethylimidazolium dicyanamide ([bmim][DCA], butylmethylimidazolium tetrafluoroborate ([bmim][$BF_4$]), butylmethylpyridinium tetrafluoroborate ([mebupyl][$BF_4$]), butylmethylimidazolium thiocyanate ([bmim][SCN]), N-butyl-4-methylpyridinium thiocyanate ([mebupyl][SCN]), 1-butyl-3-methylimidazolium nitrate ([bmim][$NO_3$]), ethylmethylimidazolium trifluoromethane sulfonate ([emim][$CF_3SO_3$]), butylmethylimidazolium methyl sulfate ([bmim][$CH_3SO_4$]), or combinations thereof.

In an embodiment, ethylmethylimidazolium bis(trifluoromethanesulfonyl)amide may comprise 1-ethyl-3-methylimidazolium bis(trifluoromethanesulfonyl)amide. In an embodiment, butylmethylimidazolium hexafluorophosphate may comprise 1-butyl-3-methylimidazolium hexafluorophosphate. In an embodiment, butylmethylimidazolium dicyanamide may comprise 1-butyl-3-methylimidazolium dicyanamide. In an embodiment, butylmethylimidazolium tetrafluoroborate may comprise 1-butyl-3-methylimidazolium tetrafluoroborate. In an embodiment, butylmethylpyridinium tetrafluoroborate ma comprise N-butyl-4-methylpyridinium tetrafluoroborate. In an embodiment, butylmethylimidazolium thiocyanate may comprise 1-butyl-3-methylimidazolium thiocyanate. In an embodiment, ethylmethylimidazolium trifluoromethanesulfonate may comprise 1-ethyl-3-methylimidazolium trifluoromethanesulfonate. In an embodiment, butylmethylimidazolium nitrate may comprise 1-butyl-3-methylimidazolium nitrate. In an embodiment, butylmethylimidazolium methylsulfate may comprise 1-butyl-3-methylimidazolium methylsulfate. In an embodiment, butylmethylpyridinium thiocyanate may comprise N-butyl-4-methylpyridinium thiocyanate.

In additional embodiments, the ionic liquid solvent may further comprise a Ag(I) salt, a Cu(I) salt, or combinations thereof.

In embodiments, the Ag(I) salt may be dissolved, dispersed, suspended, or combinations thereof in the ionic liquid solvent. When dissolved, dispersed, suspended, or combinations thereof, the Ag(I) salt may form a Ag(I) cation in the ionic liquid solvent. The Ag(I) salt may comprise silver(I) bis(trifluoromethanesulfonyl)amide ([Ag(I)][$Tf_2N$]), silver (I) trifluoromethanesulfonate ([Ag(I)][TfO]), silver(I) nitrate ([Ag(I)][$NO_3$]), or combinations thereof. In embodiments, a concentration of silver (e.g., Ag(I)) in the ionic liquid solvent is from 0 N to about 5 N; alternatively, from about 0.45N to about 1.8 N. The disclosed embodiments also include ionic liquid solvents which have no silver salt and comprise one or more of the ionic liquids disclosed herein.

In embodiments, the Cu(I) salt may be dissolved, dispersed, suspended, or combinations thereof in the ionic liquid solvent. When dissolved, dispersed, suspended, or combinations thereof, the Cu(I) salt may form a Cu(I) cation in the ionic liquid solvent. The Cu(I) salt may comprise copper(I) chloride ([Cu(I)][Cl]), copper(I) bromide ([Cu(I)][Br]), cuprous trifluoroacetate ([Cu(I)][TFA]), copper(I) nitrate ([Cu(I)][$NO_3$]), or combinations thereof. In embodiments, a concentration of copper (e.g., Cu(I)) in the ionic liquid solvent is from 0 N to about 5 N; alternatively, from about 0.45N to about 1.8 N. The disclosed embodiments also include ionic liquid solvents which have no copper salt and comprise one or more of the ionic liquids disclosed herein.

Not intending to be bound by theory, embodiments of the ionic liquid solvent disclosed herein may interact with the double carbon bonds of a gaseous component (e.g., an olefin). In an embodiment, capture of at least a portion of the gaseous component (optionally, at least a portion of the second gaseous component) may comprise reversibly complexing, binding, linking, bonding, interacting, dissolving or combinations thereof the gaseous component (optionally, second gaseous component) with the ionic liquid solvent, for example, via the formation of a complex, a link, a bond, an attraction, an interaction, a solution or combinations thereof. For example, an olefin (e.g., ethylene) may complex with a Ag(I) cation and/or a Cu(I) cation of an ionic liquid solvent to form a captured olefin (e.g., ethylene) complex.

In embodiments, the ionic liquid solvents disclosed herein may be selective to the gaseous component (optionally, the second gaseous component) over one or more fluid components in the process stream 111. For example, the ionic liquid solvents disclosed herein may be selective to ethylene over ethane, may be selective to isobutane over ethane, may be selective to $CO_2$ over natural gas, may be selective to $CO_2$ over syngas, may be selective to $H_2S$ over natural gas, or combinations thereof.

In embodiments, the selectivity of the ionic liquid solvent to the gaseous component (optionally, the second gaseous component) over one or more fluid components in the process stream 111 may be from about 8 to greater than about 300. For example, the selectivity of ethylene to ethane, isobutane to ethane, $CO_2$ to natural gas or syngas, $H_2S$ to natural gas, or combinations thereof may be from about 8 to greater than about 300.

In an embodiment, the ionic liquid solvent may reversibly capture (e.g., absorb, adsorb, dissolve, complex or combinations thereof) and/or induce the capture of the gaseous component (e.g., ethylene, $CO_2$) from the process stream 111 comprising various other fluids (e.g., gases). In an additional or alternative embodiment, the ionic liquid solvent may reversibly capture (e.g., absorb, adsorb, dissolve, complex or combinations thereof) and/or induce the capture of the second gaseous component (e.g., isobutane, $H_2S$) from the process stream 111. In an additional or alternative embodiment, the ionic liquid solvent may reversibly capture (e.g., absorb, adsorb, dissolve, complex or combinations thereof) and/or induce the capture of the second gaseous component (e.g., isobutane, $H_2S$) in addition to the gaseous component (e.g., ethylene, $CO_2$) from the process stream 111.

In embodiments, the flow of the process stream 111 components relative to the ionic liquid solvent in the separator 110 may be concurrent, countercurrent, or staged in sections of the separator 110.

In embodiments, components and/or portions of components of process stream 111 which are not captured by the ionic liquid solvent (e.g., in embodiments where at least a portion of the second gaseous component is not captured, where a third gaseous component is not captured) may flow exit the separator 110 and flow through uncaptured stream 112. In embodiments, the uncaptured stream 112 may comprise hydrogen, nitrogen, ethane, isobutane, or combinations thereof. In alternative embodiments, the uncaptured stream 112 may comprise syngas. In alternative embodiments, the uncaptured stream 112 may comprise natural gas. One or more of the components in the uncaptured stream 112 be further processed according to techniques known in the art, one or more components of the uncaptured stream 112 may be flared, or combinations thereof. In the embodiment of system 200 shown in FIG. 2, the uncaptured second gaseous component may be recovered via a membrane unit 130 (discussed in detail below).

In embodiments, at least a portion of the gaseous component (optionally, at least a portion of the second component) may exit from the separator 110 and flow to the regenerator 120 via captured stream 113. Captured stream 113 may comprise the ionic liquid solvent, captured portions of the gaseous component (e.g., ethylene, $CO_2$), captured portions of the second gaseous component (e.g., isobutane, $H_2S$), or combinations thereof.

In embodiments, the regenerator 120 may comprise one or more vessels (e.g., in series, in parallel, or both) configured to regenerate the ionic liquid solvent, to liberate at least a portion of the captured gaseous component, to liberate at least a portion of the captured second gaseous component, or combinations thereof. In an embodiment, regenerator 120 may be heated to liberate the gaseous component (optionally, the second gaseous component) from the ionic liquid solvent so as to regenerate the ionic liquid solvent using one or more heat sources comprising cooling water, low-pressure steam, or combinations thereof.

In an embodiment, regenerator 120 may be configured to operate on the basis of a temperature suitable to liberate (e.g., change a solubility, vaporize, desorb) the captured gaseous component (optionally, second gaseous component) from the ionic liquid solvent in the regenerator 120. In embodiments, the regenerator 120 may operate at a temperature greater than a temperature of the separator 110, a temperature from about 60° C. to about 450° C., or combinations thereof. In additional or alternative embodiments, the regenerator 120 may operate at a temperature from about 93° C. to about 204° C.; alternatively, from about 93° C. to about 149° C.; alternatively, from about 149° C. to about 204° C.

In an embodiment, regenerator 120 may be configured such that the components of the captured stream 113 experience a pressure differential when entering the regenerator 120. In such an embodiment, the regenerator 120 may be configured to provide or maintain a suitable pressure suitable to liberate (e.g., change a solubility, vaporize, desorb) the captured gaseous component (optionally, second gaseous component) from the ionic liquid solvent in the regenerator 120. In embodiments, the regenerator 120 may operate at a pressure less than (e.g., about 20 psia less than) a pressure at which the separator 110 operates, a pressure greater than or equal to about 14.7 psia, or combinations thereof. In additional or alternative embodiment, the regenerator 120 may operate at a pressure greater of about 16 psia or about 50 psia.

In embodiments, the regenerator 120 may comprise a series of vessel which operate via pressure differential, wherein each of the vessels in the series operates at the same or different pressures. For example, the regenerator 120 may comprise two vessels in series in which the first vessel operates at a pressure disclosed herein for the regenerator 120, and the second vessel operates at a pressure disclosed herein for the regenerator 120 which is lower than the pressure of the first vessel.

In an embodiment, the regenerator 120 may be configured for batch and/or continuous processes. For example, the regenerator 120 may operate in traditional batch or continuous operations. In another example, two or more regenerators may operate in batch mode and alternate in operation such that regeneration of the ionic liquid solvent in the system 100 is continuous.

In the regenerator 120, the captured gaseous component(s) (e.g., gaseous component and, optionally, second gaseous component) of captured stream 113 may separate to form a recovered stream 121 comprising the recovered gaseous component (optionally, recovered second gaseous component) and a solvent stream 122 comprising the regenerated ionic liquid solvent. By "regenerated," it is meant that at least a majority of the captured gaseous component (optionally, second gaseous component) is liberated from the ionic liquid solvent in the regenerator 120. Liberating may include reversing a complex, breaking a bond, reversing an interaction, reversing an attraction, reversing a dissolution, desorbing, or combinations thereof. The recovered gaseous component (optionally, the second recovered gaseous component) may be emitted from the regenerator 120 via recovered stream 121.

The solvent stream 122 may comprise regenerated ionic liquid solvent which flows from the regenerator 120 to the separator 110. The regenerated ionic liquid solvent may be circulated for reuse in the separator 110. The regenerated ionic liquid solvent may be referred to as a "lean solvent."

The recovered stream 121 may comprise the recovered gaseous component (optionally, second gaseous component). The recovered stream 121 may be introduced into or reused in processes such as a polyethylene polymerization process; the recovered stream 121 may be collected for further processing (e.g., cracking, catalytic cracking, pyrolysis, dehydrogenating, deoxygenating, scrubbing, converting, treating, or combinations thereof); the recovered stream 121 may be used for distribution, sale, etc., of the gaseous component (optionally, second gaseous component); the recovered stream 121 may be used as fuel; or combinations thereof.

In embodiments, the recovered stream 121 may comprise substantially (e.g., >90% by weight of the recovered stream 121) the recovered gaseous component (e.g., olefin, acid gas). In additional or alternative embodiments, the recovered stream 121 may comprise substantially (e.g., >90% by weight of the recovered stream 121) the recovered gaseous component (e.g., olefin, acid gas) and the recovered second gaseous component (e.g., alkane, acid gas).

In embodiments, the recovered stream 121 may comprise greater than about 50%, 60%, 70%, 80%, 85%, 90%, 95%, or more, of the gaseous component (e.g., olefin, acid gas) recovered from the process stream 111. In additional or alternative embodiments, the recovered stream 121 may comprise greater than about 50%, 60%, 70%, 80%, 85%, 90%, 95%, or more, of the second gaseous component (e.g., alkane, acid gas) recovered from the process stream 111.

In particular embodiments, the recovered stream 121 may comprise greater than about 85%, 90%, 95%, or more of the olefin (e.g., ethylene) recovered from the process stream 111. In additional or alternative embodiments, the recovered stream 121 may comprise greater than about 80%, 85%, 90%, 95%, or more, of the alkane recovered from the process stream 111. In alternative embodiments, the recovered stream 121 may comprise greater than about 50%, 60%, 70%, 80%, 90%, or more, of the $CO_2$ recovered from the process stream 111. In additional or alternative embodiments, the recovered stream 121 may comprise greater than about 50%, 60%, 70%, 80%, 90%, or more, of the $H_2S$ recovered from the process stream 111.

In embodiments, the purity of the recovered gaseous component (e.g., olefin, acid gas) in the recovered stream 121 may be greater than about 50%, 60%, 70,%, 80%, 90%, 95%, 96%, 97,%, 98%, 99%, or more, by weight of the recovered stream 121. In additional or alternative embodiments, the purity of the recovered second gaseous component (e.g., alkane, acid gas) in the recovered stream 121 may be greater than 50%, 60%, 70,%, 80%, 90%, 95%, 96%, 97,%, 98%, 99%, or more, by weight of the recovered stream 121. In particular embodiments, the recovered stream 121 may comprise substantially (e.g., >90 wt % by weight of the recovered stream 121) olefin (e.g., ethylene); alternatively, the recovered stream 121 may comprise substantially (e.g., >90 wt % by weight of the recovered stream 121) olefin (e.g., ethylene) and alkane (e.g., isobutane); alternatively, the recovered stream 121 may comprise substantially (e.g., >90 wt % by weight of the recovered stream 121) $CO_2$; alternatively, the recovered stream 121 may comprises substantially (e.g., >90 wt % by weight of the recovered stream 121) of $CO_2$ and $H_2S$.

The recovered stream 121 may further comprise other fluid components such as hydrogen, nitrogen, methane, ethane, propylene, propane, heavier hydrocarbons, or combinations thereof. Such components may be present in recovered stream 121 in various amounts due to capture of the fluid component by the ionic liquid solvent; however, the presence of one or more other fluid components in the recovered stream 121 is at levels lower than the gaseous component (optionally, second gaseous component) disclosed herein such that the recovery and purity levels of the gaseous component (optionally, second gaseous component) are met.

Figure 2:
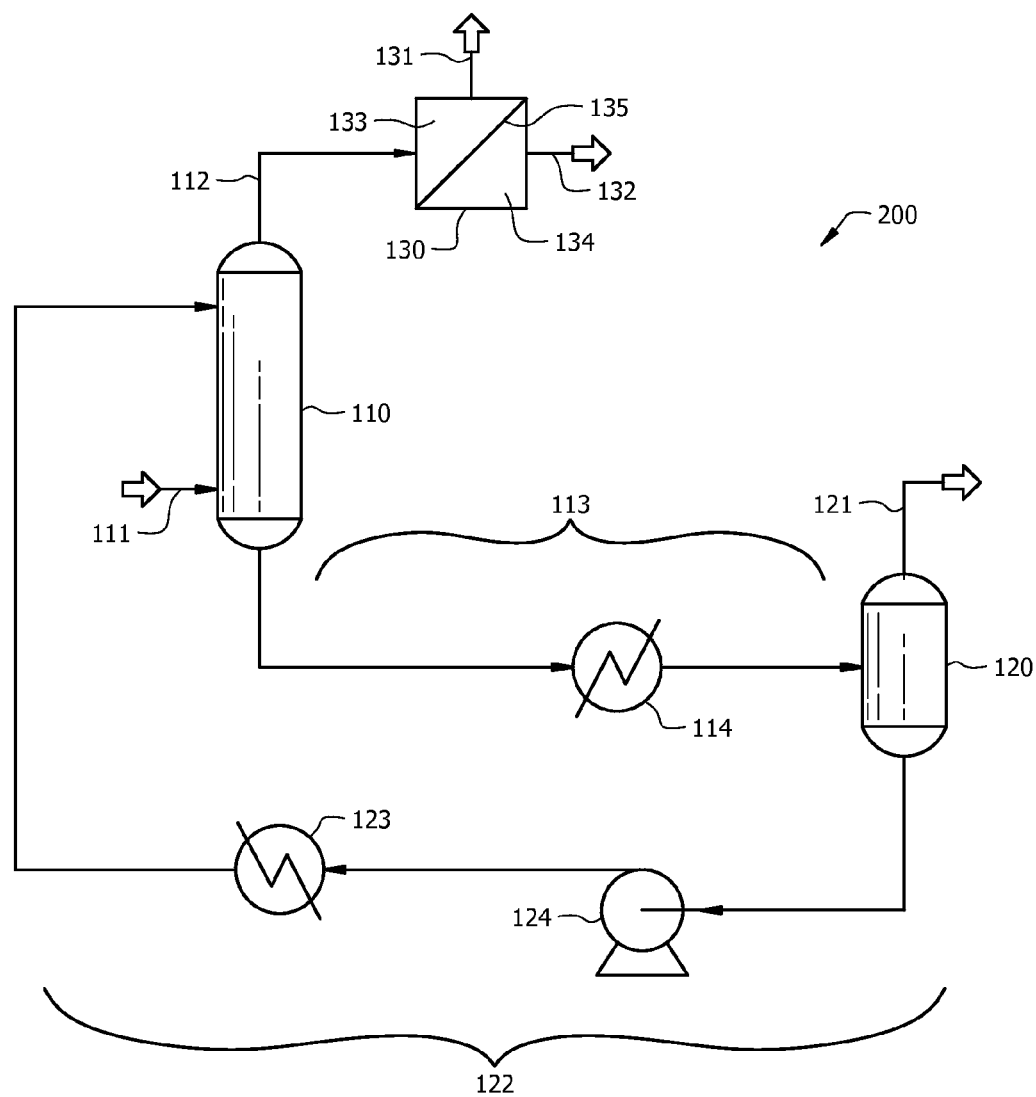
FIG. 2 illustrates a process flow diagram of another embodiment of the disclosed system.

FIG. 2 shows a process flow diagram of another embodiment of the disclosed system 200. As can be seen, the system 200 of FIG. 2 may comprise the same components (e.g., separator 110, regenerator 120, heater 114, cooler 123, pump 124, solvent circulation system, process stream 111, captured stream 113, solvent stream 122, recovered stream 121) as the system 100 of FIG. 1. System 200 further comprises a membrane unit 130 and associated streams 131 and 132. Uncaptured gaseous components which are not captured in the separator 110 by the ionic liquid solvent may exit from the separator 110 and flow through uncaptured stream 112 to the membrane unit 130 for further processing.

Generally, the separator 110 may capture a gaseous component of the process stream 111 (as described for FIG. 1 above), and uncaptured components of the process stream 111 (uncaptured in the separator 110) may exit from the separator 110 and flow to the membrane unit 130 via uncaptured stream 112 (as described for FIG. 1 above). The membrane unit 130 may comprise a membrane 135 which is selective to one or more fluid components (e.g., a second gaseous component) of the process stream 111. Uncaptured stream 112 feeds uncaptured components to the membrane unit 130. Uncaptured stream 112 may comprise various equipment (e.g., compressor, pump, valve, heat exchanger, or combinations thereof) which may can alter the conditions (e.g., temperature, pressure, phase) of the uncaptured stream 112 for flow of uncaptured gaseous components to the membrane unit 130. One or more of the uncaptured components may selectively permeate through the membrane 135 to the permeate side 134 of the membrane 135. The portions of the uncaptured components which do not permeate through the membrane 135 may comprise the retentate of the membrane 135 on the retentate side 133 of the membrane 135. The permeate may flow from the permeate side 134 of the membrane 135 and through permeate stream 132 for further processing, use, flare, disposal, or sale. The retentate may flow from the retentate side 133 of the membrane 135 and through retentate stream 131 for further processing, use, flare, disposal, or sale.

In embodiments, the membrane 135 of the membrane unit 130 is selective to alkanes (e.g., isobutane, ethane), $H_2S$, nitrogen, hydrogen, or combinations thereof. Membrane units having membranes which are selective to one or more of the uncaptured components are known in the art. For example, membrane units suitable for removal of $H_2S$ in system 200 are disclosed in U.S. Pat. Nos. 5,556,449; 5,558, 698; 5,407,467; 5,401,300; and 6,572,678, each of which is incorporated herein by reference in its entirety. Membrane units suitable for removal of hydrogen in system 200 are disclosed in U.S. Pat. Nos. 6,555,316 and 5,980,609, each of which is incorporated herein by reference in its entirety. Membrane units suitable for removal of alkanes in system 200 are disclosed in U.S. Pat. No. 5,980,609, which is incorporated herein by reference in its entirety. Membrane units suitable for removal of nitrogen in system 200 are disclosed in U.S. Pat. No. 7,479,227, which is incorporated herein by reference in its entirety.

In embodiments, the membrane unit 130 may comprise two or more membrane units which include two or more membranes having the same or different selectivity as one another. For example, an alkane-selective membrane may be used to recover an uncaptured alkane in combination with a nitrogen-selective membrane. In another example, multiple membrane units may be used which are selective to $H_2S$ to achieve low levels of $H_2S$.

Operation of the system 200 shown in FIG. 2 may include, but is not limited to, two operational embodiments. First, at least a portion of a gaseous component of the process stream 111 may be captured by the ionic liquid solvent in the separator 110 while at least a portion of a second gaseous component of the process stream 111 is not captured, exits from the separator 110, and flows to the membrane unit 130 via uncaptured stream 112. The uncaptured portion of the second gaseous component is then recovered from the membrane unit 130, and at least a portion of the captured gaseous component is recovered either from the separator 110 (e.g., in embodiments where the separator provides a dual function as a regenerator) or from the regenerator 120 of FIG. 2. Second, at least a portion of a gaseous component and at least a portion of a second gaseous component of the process stream 111 may be captured by the ionic liquid solvent in the separator 110 while at least a portion of a third gaseous component of the process stream 11 is not captured, exits from the separator 110, and flows to the membrane unit 130 via uncaptured stream 112. The uncaptured portion of the third gaseous component is then recovered from the membrane unit 130, and the captured portion of the gaseous component and captured portion of the second gaseous component are recovered either from the separator 110 (e.g., in embodiments where the separator 110 provides a dual function as a regenerator) or from the regenerator 120 shown in FIG. 2.

In system 200, the process stream 111, captured stream 113, uncaptured stream 112, solvent stream 122, and recovered stream 121 may comprise embodiments of the process stream 111, captured stream 113, uncaptured stream 112, solvent stream 122, and recovered stream 121 described for the system 100 of FIG. 1 Likewise, the separator 110 and regenerator 120 of system 200 may comprise embodiments of the separator 110 and regenerator 120 of system 100 described for FIG. 1.

In system 200, depending upon the selectivity of the membrane 135, retentate stream 131 or permeate stream 132 may comprise the recovered second gaseous component or the recovered third gaseous component. The retentate stream 131 or permeate stream 132 may be introduced into or reused in processes such as a polyethylene polymerization process; retentate stream 131 and/or permeate stream 132 may be collected for further processing (e.g., cracking, catalytic cracking, pyrolysis, dehydrogenating, deoxygenating, scrubbing, converting, treating, or combinations thereof); retentate stream 131 or permeate stream 132 may be used for distribution, sale, etc., of the second gaseous component (optionally, third gaseous component); the retentate stream 131 or permeate stream 132 may be used as fuel; or combinations thereof.

In embodiments, the retentate stream 131 or permeate stream 132 may comprise substantially (e.g., >90% by weight of the retentate stream 131 or permeate stream 132) the recovered second gaseous component (e.g., alkane, acid gas). In additional or alternative embodiments, the retentate stream 131 or permeate stream 132 may comprise substantially (e.g., >90% by weight of the retentate stream 131 or permeate stream 132) the recovered third gaseous component (e.g., alkane, nitrogen, hydrogen, acid gas).

In embodiments, the retentate stream 131 or permeate stream 132 may comprise greater than about 50%, 60%, 70%, 80%, 85%, 90%, 95%, or more, of the second gaseous component (e.g., alkane, acid gas) recovered from the process stream 111. In additional or alternative embodiments, the retentate stream 131 or permeate stream 132 may comprise greater than about 50%, 60%, 70%, 80%, 85%, 90%, 95%, or more, of the third gaseous component (e.g., alkane, acid gas, hydrogen, nitrogen, natural gas, syngas) recovered from the process stream 111.

In particular embodiments, the retentate stream 131 or permeate stream 132 may comprise greater than about 80%, 85%, 90%, 95%, or more, of the alkane recovered from the process stream 111. In alternative embodiments, the retentate stream 131 or permeate stream 132 may comprise greater than about 50%, 60%, 70%, 80%, 90%, or more, of the natural gas or syngas recovered from the process stream 111. In additional or alternative embodiments, the retentate stream 131 or permeate stream 132 may comprise greater than about 50%, 60%, 70%, 80%, 90%, or more, of the $H_2S$ recovered from the process stream 111.

In embodiments, the purity of the recovered second gaseous component (e.g., alkane, acid gas) in the retentate stream 131 or permeate stream 132 may be greater than about 50%, 60%, 70,%, 80%, 90%, 95%, 96%, 97,%, 98%, 99%, or more, by weight of the retentate stream 131 or permeate stream 132. In additional or alternative embodiments, the purity of the recovered third gaseous component (e.g., alkane, acid gas, hydrogen, nitrogen, natural gas, syngas) in the retentate stream 131 or permeate stream 132 may be greater than 50%, 60%, 70,%, 80%, 90%, 95%, 96%, 97,%, 98%, 99%, or more, by weight of the retentate stream 131 or permeate stream 132. In particular embodiments, the retentate stream 131 or permeate stream 132 may comprise substantially (e.g., >90 wt % by weight of the retentate stream 131 or permeate stream 132) alkane (e.g., isobutane, ethane, propane); alternatively, the retentate stream 131 or permeate stream 132 may comprise substantially (e.g., >90 wt % by weight of the retentate stream 131 or permeate stream 132) natural gas or syngas; alternatively, the retentate stream 131 or permeate stream 132 may comprise substantially (e.g., >90 wt % by weight of the retentate stream 131 or permeate stream 132) of $CO_2$ and/or $H_2S$.

In embodiments of the system 200, the gaseous component may comprise an olefin (e.g., ethylene) or an acid gas ($CO_2$ or $H_2S$); the second gaseous component may comprise an alkane (e.g., isobutane) or an acid gas ($CO_2$ or $H_2S$); the third gaseous component may comprise an alkane (e.g., ethane), natural gas, syngas, hydrogen, or nitrogen.

The disclosed embodiments include methods for recovering at least a portion of a gaseous component (e.g., the gaseous component, second gaseous component, third gaseous component, or combinations thereof, as described above).

In an embodiment, a method comprises providing a process stream comprising a gaseous component, capturing at least a portion of the gaseous component from the process stream by the ionic liquid solvent, and recovering at least a portion of a captured gaseous component from the ionic liquid solvent. In additional embodiments, the process stream comprises a second gaseous component and at least a portion of the second gaseous component from the process stream is captured by the ionic liquid solvent, and the method further comprises recovering at least a portion of the second gaseous component from the ionic liquid solvent.

In embodiments of the method, the ionic liquid solvent may comprise a cation, an anion, a Ag(I) salt, a Cu(I) salt, or combinations thereof.

In embodiments of the method, the cation may comprise an ethylmethylimidazolium [emim] cation, a butylmethylimidazolium [bmim] cation, a butylmethylpyridinium [mebupyl] cation, or combinations thereof. In embodiments, the anion may comprise a bis(trifluoromethanesulfonyl)amide [Tf$_2$N] anion, a hexafluorophosphate [PF$_6$] anion, a trifluoromethanesulfonate [TfO] anion, a dicyanamide [DCA] anion, a tetrafluoroborate [BF$_4$] anion, a thiocyanate [SCN] anion, a nitrate [NO$_3$] anion, a sulfonate [CF$_3$SO$_3$] anion, a methylsulfate [CH$_3$SO$_4$] anion, or combinations thereof.

In embodiments of the method, the ionic liquid solvent may comprise ethylmethylimidazolium bis(trifluoromethanesulfonyl)amide, butylmethylimidazolium hexafluorophosphate, ethylmethylimidazolium trifluoromethanesulfonate, ethylmethylimidazolium dicyanamide, butylmethylimidazolium dicyanamide, butylmethylimidazolium tetrafluoroborate, butylmethylpyridinium tetrafluoroborate, butylmethylimidazolium thiocyanate, ethylmethylimidazolium trifluoromethanesulfonate, butylmethylimidazolium nitrate, ethylmethylimidazolium trifluoromethane sulfonate, butylmethylimidazolium methylsulfate, butylmethylpyridinium thiocyanate, or combinations thereof.

In embodiments of the method, the Ag(I) salt may comprise silver(I) bis(trifluoromethanesulfonyl)amide ([Ag(I)][Tf$_2$N]), silver(I) trifluoromethanesulfonate ([Ag(I)][TfO]), silver(I) nitrate ([Ag(I)][NO$_3$]), or combinations thereof. In embodiments of the method, the concentration of silver in the ionic liquid solvent may comprise 0 N to about 5 N; alternatively, 0 N to about 2 N; alternatively, about 0 N to about 1.8 N; alternatively, about 0.45 N to about 1.8 N; alternatively, the concentration of silver in the ionic liquid solvent is zero.

In embodiments of the method, the Cu(I) salt may comprise copper(I) chloride ([Cu(I)][Cl]), copper(I) bromide ([Cu(I)][Br]), cuprous trifluoroacetate ([Cu(I)][TFA]), copper(I) nitrate ([Cu(I)][NO$_3$]), or combinations thereof. In embodiments of the method, a concentration of copper (e.g., Cu(I)) in the ionic liquid solvent is 0 N to about 5 N; alternatively, 0 N to about 2 N; alternatively, about 0 N to about 1.8 N; alternatively, about 0.45 N to about 1.8 N; alternatively, the concentration of copper in the ionic liquid solvent is zero.

In embodiments of the method, the step of capturing may be performed at a liquid-to-gas mass flow ratio from about 1 to about 350; alternatively, from about 1 to about 200; alternatively, from about 10 to about 200; alternatively, from about 10 to about 100. In additional or alternative embodiments, the step of capturing may be performed at a liquid-to-gas mass flow ratio such that at least a portion of a second gaseous component is captured by the ionic liquid solvent in addition to the capture of the gaseous component. In such embodiments, the liquid-to-gas mass flow ratio may comprise greater than about 10; alternatively, greater than about 15. In additional or alternative embodiments, the step of capturing may be performed at a liquid-to-gas mass flow ratio such that at least a portion of the second gaseous component is not captured by the ionic liquid solvent. In such embodiments, the liquid-to-gas mass flow ratio may comprise less than about 200.

In embodiments, the method may further comprise flowing the ionic liquid solvent at a mass flow rate from about 1,000 pounds per hour to about 300,000 pounds per hour. In additional or alternative embodiments, the method may further comprise flowing the ionic liquid solvent at a flow rate which captures at least a portion of the gaseous component, wherein the gaseous component comprises an acid gas.

In embodiments, the gaseous component and/or are the second gaseous component are captured by absorption, adsorption, dissolution, complexation, or combinations thereof.

In embodiments, the method may further comprise flowing an uncaptured portion of the second gaseous component to a membrane unit, and recovering at least a portion of the uncaptured portion of the second gaseous component from the membrane unit. In additional embodiments, the method may comprise flowing an uncaptured portion of a third gaseous component to the membrane unit, and recovering at least a portion of the uncaptured portion of the third gaseous component from the membrane unit.

In embodiments of the method, the step of capturing may be performed at a temperature from about 5° C. to about 50° C.; alternatively, about 20° C. to about 40° C. In embodiments of the method, the step of capturing may be performed at a pressure from about 100 psia to about 250 psia.

In embodiments of the method, recovering at least a portion of the captured gaseous component, the captured second gaseous component, or combinations thereof, may be performed at a temperature greater than a temperature at which the gaseous component, the second gaseous component, or combinations thereof, is captured; additionally or alternatively, from about 60° C. to about 450° C.

In embodiments of the method, recovering at least a portion of the captured gaseous component, the captured second gaseous component, or combinations thereof, may be performed at a pressure less than a pressure at which the gaseous component, the second gaseous component, or combinations thereof, is captured; at a pressure greater than about 14.7 psia; at a pressure which is about 20 psia less than the pressure at which the gaseous component, the second gaseous component, or combinations thereof, is captured; or combinations thereof.

In embodiments of the method, recovering at least a portion of the captured gaseous component, of the captured second gaseous component, or combinations thereof, may comprise liberating at least a portion of the captured gaseous component, of the captured second gaseous component, or combinations thereof, from the ionic liquid solvent, and recovering the liberated gaseous component, the liberated second gaseous component, or combinations thereof. Liberating the captured gaseous component and/or the captured second gaseous component from the ionic liquid solvent may generally comprise any suitable means of reversing the various links, bonds, attractions, interactions, complexes, or combinations thereof by which the captured gaseous component (optionally, captured second gaseous component) is bound, linked, bonded or combinations thereof to the ionic liquid solvent. Nonlimiting examples of a suitable means by which to liberate the captured gaseous component (optionally, captured second gaseous component) include altering a solubility of a captured gaseous component(optionally, captured second gaseous component), altering absorption kinetics or the absorption equilibrium of the ionic liquid solvent, heating the ionic liquid solvent comprising a captured gaseous component (optionally, captured second gaseous component), depressurizing the ionic liquid solvent comprising a captured gaseous component (optionally, captured second gaseous component), altering the partial pressure of the captured gaseous component (optionally, captured second gaseous component), or combinations thereof. In an embodiment, liberating the captured gaseous component (optionally, captured second gaseous component) may comprise depressurizing the ionic liquid solvent comprising the captured gaseous component (optionally, captured second gaseous component) to a suitable partial pressure. In an additional embodiment, liberating the captured gaseous component (optionally, captured second gaseous component) may comprise heating the ionic liquid solvent comprising the captured gaseous component (optionally, captured second gaseous component) within a separator or regenerator to a suitable temperature. Such a suitable temperature may be at a temperature greater than a temperature at which the gaseous component, the second gaseous component, or combinations thereof, is captured; alternatively or additionally, at a temperature from about 60° C. to about 450° C., to encourage release of the captured component from the ionic liquid solvent.

In embodiments of the method, the gaseous component may comprise an olefin or an acid gas, and the second gaseous component may comprise an alkane or an acid gas. The olefin may comprise ethylene, the alkane may comprise isobutane, and the acid gas may comprise $CO_2$ or $H_2S$.

EXAMPLES

The disclosure having been generally described, the following examples are given as particular embodiments of the disclosure and to demonstrate the practice and advantages thereof. It is understood that these examples are given by way of illustration and is not intended to limit the specification or the claims in any manner.

A commercial process simulator was employed to generate models in accordance with the systems and/or methods disclosed herein. The models employed a system as shown in the figures. In the models, a process stream 111 feeds to the separator 110. As is seen below, using an ionic liquid solvent as disclosed herein for the capture of gaseous components provides for high selectivity of the gaseous component to other components in the process stream 111.

Example 1

Example 1 utilizes the system 100 of FIG. 1. Process stream 111 of FIG. 1 is fed to the bottom of the separator 110. The composition and conditions for the process stream 111 of Example 1 are given in Table 1 below:

TABLE 1

| Composition | Mass flow (lb/hr) | Molar flow (kmol/hr) | Molar fraction | Partial pressure (psia) |
|---|---|---|---|---|
| Hydrogen | 31.06 | 7.1 | 0.29 | 59.3 |
| Nitrogen | 136.53 | 2.2 | 0.09 | 18.6 |

TABLE 1-continued

| Composition | Mass flow (lb/hr) | Molar flow (kmol/hr) | Molar fraction | Partial pressure (psia) |
|---|---|---|---|---|
| Ethane | 169.14 | 2.6 | 0.11 | 21.5 |
| Ethylene | 728.54 | 11.8 | 0.49 | 99.4 |
| I-Butane | 62.04 | 0.5 | 0.02 | 4.1 |
| Total | 1127.31 | 24.2 | 1.00 | 203.0 |

Solvent stream 122 comprising the ionic liquid solvent is fed to the top of the separator 110. The pressure of the separator 110 is about 186 psia, and the temperature is about 30° C. The ionic liquid solvent is [emim][$Tf_2N$]—Ag, and the concentration of Ag(I) in the ionic liquid solvent is about 1.8 N.

In the separator 110, gaseous hydrogen, nitrogen, ethane, ethylene and isobutane rise through the ionic liquid solvent, and ethylene is captured (via absorption and complexing as described herein) into the [emim][$Tf_2N$]—Ag while isobutane is physisorbed. The ethylene which is complexed with the [emim][$Tf_2N$]—Ag and isobutane which is physisorbed in [emim][$Tf_2N$] exits from the separator 110 and flows to a regenerator 120 via captured stream 113. Ethylene liberates (e.g., desorbs) and the isobutane liberates from the [emim][$Tf_2N$]—Ag in the regenerator 120, where the pressure is about 16 psia and temperature is about 93° C., so as to regenerate the [emim][$Tf_2N$]—Ag and provide a recovered stream 121 comprising ethylene and isobutane. The regenerated [emim][$Tf_2N$]—Ag is recycled back to the separator 110 via solvent stream 122.

For a solvent stream 122 flow rate of 225,400 lb/hr, and a mass flow ratio of liquid to gas of about 200, ethylene recovery in recovered stream 121 is about 96.5% by weight of ethylene in the process stream 111 or by moles of ethylene in the process stream 111, isobutane recovery is about 88% by weight of isobutane in the process stream 111 or by moles of isobutane in the process stream 111, and the purity of the recovered ethylene and isobutane is about 90% by mole of ethylene and isobutane in the recovered stream 121.

Example 1 demonstrates an ionic liquid solvent as disclosed herein can selectively capture two gaseous components of the process stream 111, i.e., in the case of Example 1, ethylene and isobutane. Moreover, the recovery of the two gaseous components is about 96.5% for ethylene and about 88% for isobutane; and the purity of the two gaseous components is about 90%. The capture of two gaseous components may avoid the need for separation of the second gaseous component (i.e., isobutane) from the process stream 111 in other equipment (i.e., in a membrane unit or other separating device). Such cases may reduce capital cost for process stream component separations and/or provide recovery of two gaseous components which may complement one another in subsequent use or sale, separations, processing, or combinations thereof.

Example 2

Example 2 utilizes the system 100 of FIG. 1. Process stream 111 of FIG. 1 comprising gaseous hydrogen, nitrogen, ethane, ethylene and isobutane is fed to the bottom of the separator 110. The composition and conditions for the process stream 111 of Example 2 are given in Table 1 above. The solvent stream 122 comprising the ionic liquid solvent is fed to the top of the separator 110.

The pressure of the separator 110 is about 186 psia, and the temperature is about 30° C. The ionic liquid solvent is [emim][Tf$_2$N]—Ag, and the concentration of Ag(I) in the ionic liquid solvent is about 1.8 N.

In the separator 110, gaseous ethane, ethylene and isobutane rise through the ionic liquid solvent, and ethylene is captured (via absorption and complexing as described herein) into the [emim][Tf$_2$N]—Ag. The ethylene which is complexed with the [emim][Tf$_2$N]—Ag exits from the separator 110 and flows to a regenerator 120 via captured stream 113. Ethylene liberates (e.g., desorbs) from the [emim][Tf$_2$N]—Ag in the regenerator 120, where the pressure is about 16 psia and temperature is about 149° C., so as to regenerate the [emim][Tf$_2$N]—Ag. The regenerated [emim][Tf$_2$N]—Ag is recycled back to the separator 110 via solvent stream 122. Recovered ethylene flows from the regenerator 120 into recovered stream 121.

For a solvent stream 122 flow rate of 16,905 lb/hr, and a mass flow ratio of liquid to gas of about 15, ethylene recovery in recovered stream 121 is about 97%, and the purity of the recovered ethylene is about 98.96%.

Example 2 demonstrates an ionic liquid solvent as disclosed herein can selectively capture one gaseous component of the process stream 111, i.e., in the case of Example 2, ethylene. Moreover, the recovery of the gaseous component is about 97% by weight of ethylene in the process stream 111, and the purity of ethylene is about 98.96% by mole of ethylene in the recovered stream 121. The selective capture of one gaseous component may avoid the need for separation of the gaseous component (i.e., ethylene) from other gaseous components subsequent to the regenerator 120. Such cases may reduce capital cost for process stream component separations and/or provide selective recovery of a gaseous component which may otherwise be difficult, expensive, or inefficient to separate from the process stream 111.

Example 3

Example 3 utilizes the system 200 of FIG. 2. Process stream 111 of FIG. 1 comprising gaseous hydrogen, nitrogen, ethane, ethylene and isobutane is fed to the bottom of the separator 110. The composition and conditions of the process stream 111 for Example 3 are shown in Table 2 below:

TABLE 2

| Composition | Mass flow (lb/hr) | Molar flow (kmol/hr) | Molar fraction | Partial pressure (psia) |
|---|---|---|---|---|
| Hydrogen | 29.7 | 6.8 | 0.46 | 88.0 |
| Nitrogen | 92.7 | 1.5 | 0.10 | 19.6 |
| Ethane | 66.7 | 1.0 | 0.07 | 13.2 |
| Ethylene | 251.5 | 4.1 | 0.28 | 53.2 |
| I-Butane | 165.4 | 1.3 | 0.09 | 16.9 |
| Total | 606 | 14.6 | 1.00 | 191.0 |

Solvent stream 122 comprising the ionic liquid solvent is fed to the top of the separator 110. The pressure of the separator 110 is about 186 psia, and the temperature is about 30° C. The ionic liquid solvent is [emim][Tf$_2$N]—Ag, and the concentration of Ag(I) in the ionic liquid solvent is about 1.8 N.

In the separator 110, gaseous ethane, ethylene and isobutane rise through the ionic liquid solvent, and ethylene is absorbed (via complexing as described herein) into the [emim][Tf$_2$N]—Ag. The ethylene which is complexed with the [emim][Tf$_2$N]—Ag exits the separator 110 and flows to a regenerator 120 via captured stream 113. Ethylene desorbs from the [emim][Tf$_2$N]—Ag in the regenerator 120, where the pressure is 16 psia and the temperature is about 149° C., so as to regenerate the [emim][Tf$_2$N]—Ag. The regenerated [emim][Tf$_2$N]—Ag is recycled back to the separator 110 via solvent stream 122.

Isobutane which is not absorbed in the separator 110 flows via stream 112 to a membrane unit 130. Isobutane is recovered as permeate of an isobutane-selective membrane 135 in the membrane unit 130. Isobutane flows from the membrane unit 130 in stream 132. Ethane and any remaining gas are recovered in the retentate of the membrane via stream 131.

For a solvent stream 122 flow rate of about 6,000 lb/hr, and a mass flow ratio of liquid to gas of about 10, ethylene recovery is about 92.6% by weight of ethylene in the process stream 111, the purity of the recovered ethylene is about 98.3% by mole of ethylene in the recovered stream 121, and isobutane recovery is as high as about 98% by weight of isobutane in the process stream 111.

Example 3 demonstrates utilization of a membrane unit 130 to recover the second gaseous component (i.e., isobutane) can provide for a smaller solvent circulation system. When compared with Examples 1 and 2, the mass flow ratio of ionic liquid solvent in Example 3 is about 10, while the mass flow ratio for Example 1 is about 200 and the mass flow ratio of Example 2 is about 15. In cases where circulation capacities to achieve mass flow ratios such as those in Examples 1 and 2 are not available (e.g., such capacity is cost-prohibitive, retrofitting for such a capacity is not possible, a footprint for such a capacity is not available, etc.), Example 3 provides for 92.6% recovery of ethylene in the separator 110 using a mass flow ratio of 10 and up to 98% recovery of isobutane in the membrane unit 130.

Prophetic Example 1

Prophetic Example 1 utilizes the system 100 of FIG. 1. Process stream 111 of FIG. 1 comprising natural gas, CO$_2$ and H$_2$S is fed to the bottom of the separator 110, and solvent stream 122 comprising the ionic liquid solvent is fed to the top of the separator 110. The mass flow ratio of liquid to gas can be about 10 to about 100. The pressure of the separator 110 is about 100 psia to about 250 psia, and the temperature is about 5° C. to about 50° C. The ionic liquid solvent is [emim][Tf$_2$N]—Ag, and the concentration of Ag(I) in the ionic liquid solvent can be 0 N to about 1.8 N.

In the separator 110, gaseous natural gas, CO$_2$, and H$_2$S rise through the ionic liquid solvent, and CO$_2$ and H$_2$S are captured (e.g., physisorb) into the [emim][Tf$_2$N]—Ag. The CO$_2$ and H$_2$S which are captured (e.g., physically dissolved) in the [emim][Tf$_2$N]—Ag exits from the separator 110 and flows to a regenerator 120 via captured stream 113. CO$_2$ and H$_2$S liberate (e.g., become insoluble) from the [emim][Tf$_2$N]—Ag in the regenerator 120 so as to regenerate the [emim][Tf$_2$N]—Ag. The regenerator 120 operates at a temperature from about 60° C. to about 450° C., and a pressure greater than or equal to about 14.7 psia where the pressure is less than about 20 psia less than the pressure of the separator 110.

The regenerated [emim][Tf$_2$N]—Ag is recycled back to the separator 110 via solvent stream 122. The CO$_2$ and H$_2$S can be recovered in recovered stream 121. The CO$_2$ recovery can be greater than 50% by weight of CO$_2$ in the process stream 111 or by mole of CO$_2$ in the process stream 111, and the H$_2$S recovery can be greater than 50% by weight of H$_2$S in the process stream 111 or by mole H$_2$S in the process stream 111. Purity of CO$_2$ in the recovered stream 121 can be greater than about 90% by mole of $CO_2$ in the recovered stream 121. Purity of $H_2S$ in the recovered stream 121 can be greater than about 90% by mole of $H_2S$ in the recovered stream 121.

Prophetic Example 1 demonstrates $CO_2$ and $H_2S$ may be removed from natural gas to provide a natural gas stream having reduced amounts of $CO_2$ and $H_2S$.

Prophetic Example 2

Prophetic Example 2 utilizes the system 100 of FIG. 1. Process stream 111 of FIG. 1 comprising syngas and $CO_2$ is fed to the bottom of the separator 110, and solvent stream 122 comprising the ionic liquid solvent is fed to the top of the separator 110. The mass flow ratio of liquid to gas can be about 10 to about 100. The pressure of the separator 110 is about 100 psia to about 250 psia, and the temperature is about 5° C. to about 50° C. The ionic liquid solvent is [emim][Tf$_2$N]—Ag, and the concentration of Ag(I) in the ionic liquid solvent can be 0 N to about 1.8 N.

In the separator 110, gaseous syngas and $CO_2$ rise through the ionic liquid solvent, and $CO_2$ is captured into the [emim][Tf$_2$N]—Ag. The $CO_2$ which is captured (e.g., physically dissolves) in the [emim][Tf$_2$N]—Ag exits from the separator 110 and flows to a regenerator 120 via captured stream 113. $CO_2$ liberates (e.g., becomes insoluble) from the [emim][Tf$_2$N]—Ag in the regenerator 120 so as to regenerate the [emim][Tf$_2$N]—Ag. The regenerator 120 operates at a temperature from about 60° C. to about 450° C., and a pressure greater than about 14.7 psia and wherein the pressure is less than about 20 psia less than the pressure of the separator 110.

The regenerated [emim][Tf$_2$N]—Ag is recycled back to the separator 110 via solvent stream 122. The $CO_2$ can be recovered in recovered stream 121. The $CO_2$ recovery can be greater than 50% by weight of $CO_2$ in the process stream 111 or by mole of $CO_2$ in the process stream 111. Purity of $CO_2$ in the recovered stream 121 can be greater than about 90% by mole of $CO_2$ in the recovered stream 121.

Prophetic Example 2 demonstrates $CO_2$ may be removed from syngas to provide a syngas stream having reduced amounts of $CO_2$.

Additional Description

A process and system for the production for polyethylene has been described. The following clauses are offered as further description:

Embodiment 1. A method comprises providing a process stream comprising a gaseous component, capturing at least a portion of the gaseous component from the process stream by the ionic liquid solvent, and recovering at least a portion of a captured gaseous component from the ionic liquid solvent.

Embodiment 2. The method of Embodiment 1, wherein at least a portion of a second gaseous component from the process stream is captured by the ionic liquid solvent, and the method further comprises recovering at least a portion of the second gaseous component from the ionic liquid solvent.

Embodiment 3. The method of one of Embodiments 1 to 2, wherein the ionic liquid solvent comprise a cation, an anion, a Ag(I) salt, a Cu(I) salt, or combinations thereof.

Embodiment 4. The method of Embodiment 3, wherein the cation comprises an ethylmethylimidazolium cation, a butylmethylimidazolium cation, a butylmethylpyridinium cation, or combinations thereof; wherein the anion comprises a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, a methylsulfate anion, or combinations thereof.

Embodiment 5. The method of one of Embodiments 3 to 4, wherein the Ag(I) salt comprises silver(I) bis(trifluoromethanesulfonyl)amide ([Ag(I)][Tf$_2$N]), silver(I) trifluoromethanesulfonate ([Ag(I)][TfO]), silver(I) nitrate ([Ag(I)][NO$_3$]), or combinations thereof.

Embodiment 6. The method of one of Embodiments 3 to 4, wherein the Cu(I) salt comprises copper(I) chloride ([Cu(I)][Cl]), copper(I) bromide ([Cu(I)][Br]), cuprous trifluoroacetate ([Cu(I)][TFA]), copper(I) nitrate ([Cu(I)][NO$_3$]), or combinations thereof.

Embodiment 7. The method of one of Embodiments 3 to 6, wherein the concentration of silver, copper, or both, in the ionic liquid solvent may comprise 0 N to about 5 N.

Embodiment 8. The method of one of Embodiments 3 to 7, wherein the concentration of silver, copper, or both, in the ionic liquid solvent may comprise 0 N to about 2 N.

Embodiment 9. The method of one of Embodiments 3 to 8, wherein the concentration of silver, copper, or both, in the ionic liquid solvent may comprise 0 N to about 1.8 N.

Embodiment 10. The method of one of Embodiments 3 to 9, wherein the concentration of silver, copper, or both in the ionic liquid solvent may comprise about 0.45 N to about 1.8 N.

Embodiment 11. The method of one of Embodiments 1 to 10, wherein said capturing may be performed at a liquid-to-gas mass flow ratio from about 1 to about 350.

Embodiment 12. The method of one of Embodiments 1 to 11, wherein said capturing may be performed at a liquid-to-gas mass flow ratio from about 10 to about 100.

Embodiment 13. The method of one of Embodiments 1 to 12, wherein said capturing may be performed at a liquid-to-gas mass flow ratio such that at least a portion of a second gaseous component is captured by the ionic liquid solvent in addition to the capture of the gaseous component.

Embodiment 14. The method of Embodiment 13, wherein the liquid-to-gas mass flow ratio comprises greater than about 10.

Embodiment 15. The method of one of Embodiments 13 to 14, wherein the liquid-to-gas mass flow ratio comprises greater than about 15.

Embodiment 16. The method of one of Embodiments 1 to 12, wherein said capturing may be performed at a liquid-to-gas mass flow ratio such that at least a portion of the second gaseous component is not captured by the ionic liquid solvent.

Embodiment 17. The method of Embodiment 16, wherein the liquid-to-gas mass flow ratio comprises less than about 200.

Embodiment 18. The method of one of Embodiments 1 to 17, further comprising flowing the ionic liquid solvent at a mass flow rate from about 1,000 pounds per hour to about 300,000 pounds per hour.

Embodiment 19. The method of one of Embodiments 1 to 18, further comprising flowing the ionic liquid solvent at a flow rate which captures at least a portion of the gaseous component, wherein the gaseous component comprises an acid gas.

Embodiment 20. The method of one of Embodiments 1 to 19, wherein the gaseous component and/or are the second gaseous component are captured by absorption, adsorption, dissolution, complexation, or combinations thereof.

Embodiment 21. The method of one of Embodiments 1 to 20, further comprising flowing an uncaptured portion of the second gaseous component to a membrane unit, and recovering at least a portion of the uncaptured portion of the second gaseous component from the membrane unit.

Embodiment 22. The method of one of Embodiments 1 to 21, further comprising flowing an uncaptured portion of a third gaseous component to the membrane unit, and recovering at least a portion of the uncaptured portion of the third gaseous component from the membrane unit.

Embodiment 23. The method of one of Embodiments 1 to 22, wherein said capturing is performed at a temperature from about 5° C. to about 50° C.

Embodiment 24. The method of one of Embodiments 1 to 23, wherein said capturing is performed at a temperature from about 20° C. to about 40° C.

Embodiment 25. The method of one of Embodiments 1 to 24, wherein said capturing is performed at a pressure from about 100 psia to about 250 psia.

Embodiment 26. The method of one of Embodiments 1 to 25, wherein recovering at least a portion of the captured gaseous component, the captured second gaseous component, or combinations thereof, is performed at a temperature greater than a temperature at which the gaseous component, the second gaseous component, or combinations thereof, is captured.

Embodiment 27. The method of one of Embodiments 1 to 26, wherein recovering at least a portion of a captured gaseous component, a captured second gaseous component, or combinations thereof, is performed at a temperature from about 60° C. to about 450° C.

Embodiment 28. The method of one of Embodiments 1 to 27, wherein recovering at least a portion of a captured gaseous component, a captured second gaseous component, or combinations thereof, is performed at a pressure less than a pressure at which the gaseous component, the second gaseous component, or combinations thereof, is captured; at a pressure greater than about 14.7 psia; at a pressure which is about 20 psia less than the pressure at which the gaseous component, the second gaseous component, or both, is captured; or combinations thereof.

Embodiment 29. The method of one of Embodiments 1 to 28, wherein recovering at least a portion of a captured gaseous component, of a captured second gaseous component, or combinations thereof, comprises liberating at least a portion of the captured gaseous component, of the captured second gaseous component, or combinations thereof from the ionic liquid solvent, and recovering the liberated gaseous component, the liberated second gaseous component, or combinations thereof.

Embodiment 30. A method comprises providing a process stream comprising an olefin, capturing at least a portion of the olefin from the process stream by an ionic liquid solvent, and recovering at least a portion of a captured olefin from the ionic liquid solvent.

Embodiment 31. The method of Embodiment 30, wherein the ionic liquid solvent comprises a cation and an anion.

Embodiment 32. The method of Embodiment 31, wherein the cation comprises an ethylmethylimidazolium cation, a butylmethylimidazolium cation, a butylmethylpyridinium cation, or combinations thereof; wherein the anion comprises a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, a methylsulfate anion, or combinations thereof.

Embodiment 33. The method of one of Embodiments 30 to 32, wherein the ionic liquid solvent comprises a Ag(I) salt, a Cu(I) salt, or combinations thereof.

Embodiment 34. The method of Embodiment 33, wherein the Ag(I) salt comprises silver(I) bis(trifluoromethanesulfonyl)amide, silver(I) trifluoromethanesulfonate, silver(I) nitrate, or combinations thereof.

Embodiment 35. The method of one of Embodiments 33 to 34, wherein the Cu(I) salt comprises copper(I) chloride, copper(I) bromide, cuprous trifluoroacetate, copper(I) nitrate, or combinations thereof.

Embodiment 36. The method of one of Embodiments 30 to 35, wherein a concentration of silver, copper, or both, in the ionic liquid solvent is from about 0.1 N to about 5 N.

Embodiment 37. The method of one of Embodiments 30 to 36, wherein the concentration of silver, copper, or both, in the ionic liquid is from about 0.45 N to about 1.8 N.

Embodiment 38. The method of one of Embodiments 30 to 37, wherein said capturing is performed at a liquid-to-gas mass flow ratio from about 1 to about 350.

Embodiment 39. The method of one of Embodiments 30 to 38, further comprising flowing the ionic liquid solvent at a mass flow rate from about 1,000 pounds per hour to about 300,000 pounds per hour.

Embodiment 40. The method of one of Embodiments 30 to 39, wherein the process stream further comprises an alkane.

Embodiment 41. The method of Embodiment 40, wherein said capturing is performed at a liquid-to-gas mass flow ratio such that at least a portion of the alkane is captured by the ionic liquid solvent in addition to the capture of at least a portion of the olefin.

Embodiment 42. The method of Embodiment 41, wherein the liquid-to-gas mass flow ratio is greater than about 15.

Embodiment 43. The method of one of Embodiments 41 to 42, wherein at least a portion of the alkane is captured by absorption, dissolution, adsorption, complexation, or combinations thereof.

Embodiment 44. The method of one of Embodiments 41 to 43, further comprising recovering at least a portion of a captured alkane from the ionic liquid solvent.

Embodiment 45. The method of Embodiment 44, wherein recovering at least a portion of a captured alkane is performed at a temperature greater than the temperature at which the alkane is captured and at a pressure less than the pressure at which the alkane is captured.

Embodiment 46. The method of Embodiment 40, wherein said capturing is performed at a liquid-to-gas mass flow ratio such that at least a portion of the alkane from the process stream is not captured by the ionic liquid solvent.

Embodiment 47. The method of one of Embodiments 40 and 46, wherein a liquid-to-gas mass flow ratio is less than about 200.

Embodiment 48. The method of Embodiment 46, further comprising flowing an uncaptured portion of the alkane to a membrane unit, and recovering at least a portion of the uncaptured portion of the alkane from the membrane unit.

Embodiment 49. The method of one of Embodiments 40 to 48, wherein the alkane comprises isobutane, wherein the olefin comprises ethylene.

Embodiment 50. The method of one of Embodiments 30 to 48, wherein the olefin comprises ethylene.

Embodiment 51. The method of one of Embodiments 30 to 50, wherein the olefin is captured by the ionic liquid solvent at a temperature from about 20° C. to about 40° C.

Embodiment 52. The method of one of Embodiments 30 to 51, wherein the olefin is captured by the ionic liquid solvent at a pressure from about 100 psia to about 250 psia.

Embodiment 53. The method of one of Embodiments 30 to 52, wherein at least a portion of the olefin is captured by absorption, adsorption, dissolution, complexation or combinations thereof.

Embodiment 54. The method of one of Embodiments 30 to 53, wherein recovering at least a portion of a captured olefin comprises liberating at least a portion of the captured olefin from the ionic liquid solvent, and recovering the liberated olefin.

Embodiment 55. The method of one of Embodiments 30 to 54, wherein recovering at least a portion of a captured olefin is performed at a temperature greater than the temperature at which the olefin is captured and at a pressure less than the pressure at which the olefin is captured.

Embodiment 56. A method comprises providing a process stream comprising an acid gas, capturing at least a portion of the acid gas from the process stream by an ionic liquid solvent, and recovering at least a portion of a captured acid gas from the ionic liquid solvent.

Embodiment 57. The method of Embodiment 56, wherein the ionic liquid solvent comprises a cation and an anion; wherein the cation comprises an ethylmethylimidazolium cation, a butylmethylimidazolium cation, a butylmethylpyridinium cation, or combinations thereof; wherein the anion comprises a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, a methylsulfate anion, or combinations thereof.

Embodiment 58. The method of one of Embodiments 56 to 57, wherein the ionic liquid solvent comprises a Ag(I), a Cu(I) salt, or combinations thereof.

Embodiment 59. The method of Embodiment 58, wherein the Ag(I) salt comprises silver(I) bis(trifluoromethanesulfonyl)amide, silver(I) trifluoromethanesulfonate, silver(I) nitrate, or combinations thereof.

Embodiment 60. The method of one of Embodiments 58 to 59, wherein the Cu(I) salt comprises copper(I) chloride, copper(I) bromide, cuprous trifluoroacetate, copper(I) nitrate, or combinations thereof.

Embodiment 61. The method of one of Embodiments 58 to 60, wherein a concentration of silver, copper, or both, in the ionic liquid solvent is from 0 N to about 2 N.

Embodiment 62. The method of one of Embodiments 56 to 61, wherein said capturing is performed at a liquid-to-gas mass flow ratio from about 10 to about 100.

Embodiment 63. The method of one of Embodiments 56 to 62, wherein said capturing is performed at a temperature from about 5° C. to about 50° C.

Embodiment 64. The method of one of Embodiments 56 to 63, wherein the captured acid gas is recovered at a temperature from about 60° C. to about 450° C.

Embodiment 65. The method of one of Embodiments 56 to 64, wherein said capturing is performed at a pressure from about 100 psia to about 250 psia.

Embodiment 66. The method of one of Embodiments 56 to 65, wherein the captured acid gas is recovered at a pressure greater than or equal to about 14.7 psia, wherein the pressure at which the captured acid gas is recovered is about 20 psia less than the pressure at which the acid gas is captured.

Embodiment 67. The method of one of Embodiments 56 to 65, further comprising flowing the ionic liquid solvent at a flow rate which captures at least a portion of the acid gas.

Embodiment 68. The method of one of Embodiments 56 to 67, wherein the acid gas comprises carbon dioxide, hydrogen sulfide, or both.

Embodiment 69. The method of one of Embodiments 56 to 68, wherein the process stream further comprises raw natural gas, syngas, or both.

Embodiment 70. The method of one of Embodiments 56 to 69, wherein the acid gas is captured by absorption, adsorption, dissolution, complexation, or combinations thereof.

Embodiment 71. A system comprising a process stream comprising a gaseous component; a separator comprising an ionic liquid solvent, wherein the separator receives the process stream, wherein the ionic liquid solvent captures at least a portion of the gaseous component; a captured stream exiting the separator and comprising the captured gaseous component captured in the ionic liquid solvent; and a regenerator to receive the captured stream, wherein the regenerator regenerates the ionic liquid solvent and emits at least a portion of a recovered gaseous component.

Embodiment 72. The system of Embodiment 71, wherein the gaseous component comprises ethylene or an acid gas; wherein the recovered gaseous component comprises ethylene or an acid gas.

Embodiment 73. The system of one of Embodiments 71 to 72, wherein the process stream further comprises a second gaseous component, wherein at least a portion of the second gaseous component is not captured in the ionic liquid solvent, the system further comprising an uncaptured stream exiting the separator and comprising an uncaptured portion of the second gaseous component, and a membrane unit to receive the uncaptured stream and to recover at least a portion of the uncaptured portion of the second gaseous components.

Embodiment 74. The system of Embodiment 73, wherein the gaseous component comprises ethylene, wherein the second gaseous components comprises isobutane.

Embodiment 75. The system of one of Embodiments 71 to 72, wherein the process stream further comprises a second gaseous component, wherein the ionic liquid solvent captures at least a portion of the second gaseous component.

Embodiment 76. The system of Embodiment 75, wherein at least a portion of the gaseous component is captured by the ionic liquid solvent via absorption, dissolution, adsorption, complexation, or combinations thereof; wherein at least a portion of the second gaseous component is captured by the ionic liquid solvent via absorption, dissolution, adsorption, complexation, or combinations thereof.

Embodiment 77. The system of one of Embodiments 75 to 76, wherein the gaseous component comprises ethylene, wherein the second gaseous component comprises isobutane.

Embodiment 78. The system of Embodiments 75 to 76, wherein the gaseous component comprises carbon dioxide; wherein the second gaseous component comprises hydrogen sulfide.

Embodiment 79. The system of one of Embodiments 75 to 78, wherein the regenerator emits at least a portion of a second recovered gaseous component.

Embodiment 80. The system of Embodiment 79, wherein the recovered gaseous component comprises ethylene or an acid gas, wherein the second recovered gaseous component comprises isobutane or an acid gas.

Embodiment 81. The system of one of Embodiments 71 to 80, wherein separator operates at a liquid-to-gas mass flow ratio from about 1 to about 350.

Embodiment 82. The system of one of Embodiments 71 to 81, wherein the separator operates at a liquid-to-gas mass flow ratio from about 10 to about 100.

Embodiment 83. The system of one of Embodiments 71 to 72 and 75 to 82, wherein the process stream further comprises a second gaseous component; wherein the ionic liquid solvent flows through the separator at a liquid-to-gas mass flow ratio such that at least a portion of the gaseous component and at least a portion of the second gaseous component are captured by the ionic liquid solvent.

Embodiment 84. The system of one of Embodiments 71 to 83, wherein the ionic liquid solvent comprises a cation and an anion; wherein the cation comprises an ethylmethylimidazolium cation, a butylmethylimidazolium cation, a butylmethylpyridinium cation, or combinations thereof; wherein the anion comprises a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, a methylsulfate anion, or combinations thereof.

Embodiment 85. The system of one of Embodiments 71 to 84, wherein the ionic liquid solvent comprises a Ag(I) salt, a Cu(I) salt, or combinations thereof.

Embodiment 86. The system of Embodiment 85, wherein the Ag(I) salt comprises silver(I) bis(trifluoromethanesulfonyl)amide, silver(I) trifluoromethanesulfonate, silver(I) nitrate, or combinations thereof.

Embodiment 87. The system of one of Embodiments 85 to 86, wherein the Cu(I) salt comprises copper(I) chloride, copper(I) bromide, cuprous trifluoroacetate, copper(I) nitrate, or combinations thereof.

Embodiment 88. The system of one of Embodiments 85 to 87, wherein a concentration of silver, copper, or both, in the ionic liquid solvent is from about 0.1 N to about 5 N.

Embodiment 89. The system of one of Embodiments 85 to 88, wherein the concentration of silver, copper, or both, in the ionic liquid is from about 0.45 N to about 1.8 N.

Embodiment 90. The system of one of Embodiments 71 to 72, wherein the process stream further comprises a second gaseous component, wherein at least a portion of the second gaseous component is not captured in the ionic liquid solvent, the system further comprising an uncaptured stream exiting the separator and comprising an uncaptured portion of the second gaseous component.

Embodiment 91. The system Embodiment 90, wherein the gaseous component comprises ethylene; wherein the second gaseous component comprises isobutane, ethane, hydrogen, nitrogen, or combinations thereof.

Embodiment 92. The system of Embodiment 90, wherein the gaseous component comprises an acid gas; wherein the second gaseous component comprises natural gas.

Embodiment 93. The system of Embodiment 90, wherein the gaseous component comprises carbon dioxide; wherein the second gaseous component comprises syngas.

Embodiment 94. The system of one of Embodiments 71 to 93, wherein the separator operates at a temperature from about 5° C. to about 50° C.

Embodiment 95. The system of one of Embodiments 71 to 94, wherein the separator operates at a temperature from about 20° C. to about 40° C.

Embodiment 96. The system of one of Embodiments 71 to 95, wherein the separator operates at a pressure from about 100 psia to about 250 psia.

Embodiment 97. The system of one of Embodiments 71 to 96, wherein the regenerator operates at a temperature greater than a temperature of the separator.

Embodiment 98. The system of one of Embodiments 71 to 97, wherein the regenerator operates at pressure less than a pressure of the separator.

Embodiment 99. The system of one of Embodiments 71 to 98, wherein the regenerator operates at a temperature from about 60° C. to about 450° C.

Embodiment 100. The system of one of Embodiments 71 to 99, wherein the regenerator operates at a pressure greater than or equal to about 14.7 psia, wherein the pressure at which the regenerator operates is about 20 psia less than a pressure at which the separator operates.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, ... 50 percent, 51 percent, 52 percent ... 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the disclosed inventive subject matter. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural or other details supplementary to the disclosure.

We claim:

1. A method comprising:
   providing a process stream comprising an acid gas;
   capturing at least a portion of the acid gas from the process stream by an ionic liquid solvent; and
   recovering at least a portion of a captured acid gas from the ionic liquid solvent,
   wherein the ionic liquid solvent comprises a Ag(I) salt, a Cu(I) salt, or combinations thereof.

2. The method of claim 1, wherein the ionic liquid solvent comprises a cation and an anion; wherein the cation comprises an ethylmethylimidazolium cation, a butylmethylimidazolium cation, a butylmethylpyridinium cation, or combinations thereof; wherein the anion comprises a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, a methylsulfate anion, or combinations thereof.

3. The method of claim 1, wherein the Ag(I) salt comprises silver(I) bis(trifluoromethanesulfonyl)amide, silver(I) trifluoromethanesulfonate, silver(I) nitrate, or combinations thereof.

4. The method of claim 1, wherein the Cu(I) salt comprises copper(I) chloride, copper(I) bromide, cuprous trifluoroacetate, copper(I) nitrate, or combinations thereof.

5. The method of claim 1, wherein a concentration of silver, copper, or both, in the ionic liquid solvent is from 0 N to about 2 N.

6. The method of claim 1, wherein said capturing is performed at a liquid-to-gas mass flow ratio from about 10 to about 100.

7. The method of claim 1, wherein said capturing is performed at a temperature from about 5° C. to about 50° C.

8. The method of claim 1, wherein the captured acid gas is recovered at a temperature from about 60° C. to about 450° C.

9. The method of claim 1, wherein said capturing is performed at a pressure from about 100 psia to about 250 psia.

10. The method of claim 1, wherein the captured acid gas is recovered at a pressure greater than or equal to about 14.7 psia, wherein the pressure at which the captured acid gas is recovered is about 20 psia less than the pressure at which the acid gas is captured.

11. The method of claim 1, further comprising:
flowing the ionic liquid solvent at a flow rate which captures at least a portion of the acid gas.

12. The method of claim 1, wherein the acid gas comprises carbon dioxide, hydrogen sulfide, or both.

13. The method of claim 1, wherein the process stream further comprises raw natural gas, syngas, or both.

14. The method of claim 1, wherein the acid gas is captured by absorption, adsorption, dissolution, complexation, or combinations thereof.

15. A system comprising:
a process stream comprising a gaseous component;
a separator comprising an ionic liquid solvent, wherein the separator receives the process stream, wherein the ionic liquid solvent captures at least a portion of the gaseous component;
a captured stream exiting the separator and comprising the captured gaseous component captured in the ionic liquid solvent; and
a regenerator to receive the captured stream, wherein the regenerator regenerates the ionic liquid solvent and emits at least a portion of a recovered gaseous component,
wherein the ionic liquid solvent comprises a Ag(I) salt, a Cu(I) salt, or combinations thereof.

16. The system of claim 15, wherein the gaseous component comprises ethylene or an acid gas; wherein the recovered gaseous component comprises ethylene or an acid gas.

17. The system of claim 15, wherein the process stream further comprises a second gaseous component, wherein at least a portion of the second gaseous component is not captured in the ionic liquid solvent, the system further comprising:
an uncaptured stream exiting the separator and comprising an uncaptured portion of the second gaseous component; and
a membrane unit to receive the uncaptured stream and to recover at least a portion of the uncaptured portion of the second gaseous components.

18. The system of claim 17, wherein the gaseous component comprises ethylene, wherein the second gaseous components comprises isobutane.

19. The system of claim 15, wherein the process stream further comprises a second gaseous component, wherein the ionic liquid solvent captures at least a portion of the second gaseous component.

20. The system of claim 19, wherein at least a portion of the gaseous component is captured by the ionic liquid solvent via absorption, dissolution, adsorption, complexation, or combinations thereof; wherein at least a portion of the second gaseous component is captured by the ionic liquid solvent via absorption, dissolution, adsorption, complexation, or combinations thereof.

21. The system of claim 19, wherein the gaseous component comprises ethylene, wherein the second gaseous component comprises isobutane.

22. The system of claim 19, wherein the gaseous component comprises carbon dioxide; wherein the second gaseous component comprises hydrogen sulfide.

23. The system of claim 19, wherein the regenerator emits at least a portion of a second recovered gaseous component.

24. The system of claim 23, wherein the recovered gaseous component comprises ethylene or an acid gas, wherein the second recovered gaseous component comprises isobutane or an acid gas.

25. The system of claim 15, wherein separator operates at a liquid-to-gas mass flow ratio from about 1 to about 350.

26. The system of claim 15, wherein the separator operates at a liquid-to-gas mass flow ratio from about 10 to about 100.

27. The system of claim 15, wherein the process stream further comprises a second gaseous component; wherein the ionic liquid solvent flows through the separator at a liquid-to-gas mass flow ratio such that at least a portion of the gaseous component and at least a portion of the second gaseous component are captured by the ionic liquid solvent.

28. The system of claim 15, wherein the ionic liquid solvent comprises a cation and an anion; wherein the cation comprises an ethylmethylimidazolium cation, a butylmethylimidazolium cation, a butylmethylpyridinium cation, or combinations thereof; wherein the anion comprises a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, a methylsulfate anion, or combinations thereof.

29. The system of claim 15, wherein the Ag(I) salt comprises silver(I) bis(trifluoromethanesulfonyl)amide, silver(I) trifluoromethanesulfonate, silver(I) nitrate, or combinations thereof.

30. The system of claim 15, wherein the Cu(I) salt comprises copper(I) chloride, copper(I) bromide, cuprous trifluoroacetate, copper(I) nitrate, or combinations thereof.

31. The method of claim 15, wherein a concentration of silver, copper, or both, in the ionic liquid solvent is from about 0.1 N to about 5 N.

32. The method of claim 31, wherein the concentration of silver, copper, or both, in the ionic liquid is from about 0.45 N to about 1.8 N.

33. The system of claim 15, wherein the process stream further comprises a second gaseous component, wherein at least a portion of the second gaseous component is not captured in the ionic liquid solvent, the system further comprising:
an uncaptured stream exiting the separator and comprising an uncaptured portion of the second gaseous component.

34. The system of claim 33, wherein the gaseous component comprises ethylene; wherein the second gaseous component comprises isobutane, ethane, hydrogen, nitrogen, or combinations thereof.

35. The system of claim 33, wherein the gaseous component comprises an acid gas; wherein the second gaseous component comprises natural gas.

36. The system of claim 33, wherein the gaseous component comprises carbon dioxide; wherein the second gaseous component comprises syngas.

37. The system of claim 15, wherein the separator operates at a temperature from about 20° C. to about 40° C.

38. The system of claim 15, wherein the separator operates at a pressure from about 100 psia to about 250 psia.

39. The system of claim 15, wherein the separator operates at a temperature from about 5° C. to about 50° C.

40. The system of claim 15, wherein the separator operates at a pressure from about 100 psia to about 250 psia.

41. The system of claim 15, wherein the regenerator operates at a temperature greater than a temperature of the separator.

42. The system of claim 15, wherein the regenerator operates at pressure less than a pressure of the separator.

43. The system of claim 15, wherein the regenerator operates at a temperature from about 60° C. to about 450° C.

44. The system of claim 15, wherein the regenerator operates at a pressure greater than or equal to about 14.7 psia, wherein the pressure at which the regenerator operates is about 20 psia less than a pressure at which the separator operates.

* * * * *